United States Patent
Buettner et al.

(10) Patent No.: US 10,023,917 B2
(45) Date of Patent: *Jul. 17, 2018

(54) HIGH RESOLUTION MELTING ANALYSIS AS A PRESCREENING TOOL

(71) Applicant: Roche Molecular Systems, Inc., Pleasanton, CA (US)

(72) Inventors: Reinhard Buettner, Villiprott (DE); Stefanie Froehner, Penzberg (DE); Sabine Merkelbach-Bruse, Aachen (DE); Jasmin Ney, Wallerfangen (DE); Angelika Roesler, Sindelsdorf (DE)

(73) Assignee: Roche Molecular Systems, Inc., Pleasanton, CA (US)

(*) Notice: Subject to any disclaimer, the term of this patent is extended or adjusted under 35 U.S.C. 154(b) by 208 days.

This patent is subject to a terminal disclaimer.

(21) Appl. No.: 14/958,567

(22) Filed: Dec. 3, 2015

(65) Prior Publication Data
US 2016/0083804 A1    Mar. 24, 2016

Related U.S. Application Data

(60) Division of application No. 14/615,877, filed on Feb. 6, 2015, now Pat. No. 9,228,239, which is a continuation of application No. 13/930,638, filed on Jun. 28, 2013, now Pat. No. 8,980,556, which is a continuation of application No. PCT/EP2012/050213, filed on Jan. 9, 2012.

(30) Foreign Application Priority Data

Jan. 11, 2011    (EP) .................................. 11150641

(51) Int. Cl.
C12Q 1/68        (2018.01)
C12Q 1/6886      (2018.01)
C12N 9/14        (2006.01)

(52) U.S. Cl.
CPC ............. *C12Q 1/6886* (2013.01); *C12N 9/14* (2013.01); *C12Q 2600/106* (2013.01); *C12Q 2600/156* (2013.01); *C12Q 2600/158* (2013.01); *C12Y 306/05002* (2013.01)

(58) Field of Classification Search
None
See application file for complete search history.

(56) References Cited

U.S. PATENT DOCUMENTS

| | | |
|---|---|---|
| 6,174,670 B1 | 1/2001 | Wittwer et al. |
| 7,387,887 B2 | 6/2008 | Wittwer et al. |
| 7,582,429 B2 | 9/2009 | Wittwer et al. |
| 2010/0112557 A1 | 5/2010 | Tobler |
| 2010/0112565 A1 | 5/2010 | Tobler |
| 2010/0304989 A1 | 12/2010 | Von Hoff et al. |

FOREIGN PATENT DOCUMENTS

| | | |
|---|---|---|
| WO | 200175160 A1 | 10/2001 |
| WO | 2006061216 A2 | 6/2006 |
| WO | 2006061216 A3 | 6/2006 |
| WO | 2008052742 A1 | 5/2008 |
| WO | 2009103790 A2 | 8/2009 |
| WO | 2010065626 A1 | 6/2010 |
| WO | 2010085826 A1 | 6/2010 |

OTHER PUBLICATIONS

Karapetis et al. (K-ras Mutations and Benefit from Cetuximab in Advanced Colorectal Cancer, N Engl J Med 2008; 359:1757-1765, Oct. 23, 2008).*
Krupuy, et al. 2006, "High resolution melting analysis for the rapid and sensitive detection of mutations in clinical samples: KRAS codon 12 and 13 mutations in non-small cell lung cancer", BMC Cancer, 6:295.
Simi, et al., 2008, "High-Resolution Melting Analysis for Rapid Detection of KRAS, BRAF, and PIK3CA Gene Mutations in Colorectal Cancer", Am J Clin Pathol, 130:247-253.
Do, et al., 2008, "High resolution melting analysis for rapid and sensitive EGFR and KRAS mutation detection in formalin fixed paraffin embedded biopsies", BMC Cancer, 8:142.
Panagiotis, et al., 2010, "PIK3CA Hotspot Mutation Scanning by a Novel and Highly Sensitive High-Resolution Small Amplicon Analysis Method", Journal of Molecular Diagnostics, 12(5).
Ma, et al., 2009, "Detection of KRAS mutations in colorectal cancer by high-resolution melting analysis", J Clin Pathol, 62:886-891.
Deschoolmeester, et al., 2010, "KRAS mutation detection and prognostic potential in sporadic colorectal cancer using high-resolution melting analysis", British Journal of Cancer, 103:1627-1636.
Willmore-Payne, et al. 2005, "Human malignant melanoma: detection of BRAF- and c-kit-activating mutations by high-resolution amplicon melting analysis", Human Pathology, 36:486-493.
Deng, et al. 2004, "BRAF Mutation is Frequently Present in Sporadic Colorectal Cancer with Methylated hMLH1, But Not in Hereditary Nonpolyposis Colorectal Cancer", Clin Cancer Res, 10:191-195.
Lopez-Knowles, et al., 2006, "PIK3CA Mutations are and Early Genetic Alteration Associated with FGFR3 Mutations in Superficial Papillary Bladder Tumors", Cancer Res, 66:7401-7404.

(Continued)

*Primary Examiner* — Aaron A Priest
(74) *Attorney, Agent, or Firm* — Carol Johns

(57) ABSTRACT

Compositions and methods for determining an increased likelihood of a response to a targeted treatment of a cancer disease including isolating genomic DNA from a patient sample, amplifying a fragment of DNA by means of PCR with a specific pair of amplification primers, determining if the amplified fragment comprises a wildtype sequence or a mutation by means of a High Resolution Melting Analysis (HRM), and correlating the presence or absence of a mutation with an increased likelihood of success of said targeted treatment. Respective primer pairs, compositions and kits are also claimed.

10 Claims, 6 Drawing Sheets

(56) References Cited

OTHER PUBLICATIONS

Assaad, et al., 2008, "Thyroidectomies from patients with history of therapeutic radiation during childhood and adolescence have a unique mutational profile", Modern Pathology, 21:1176-1182.
BIO-RAD, 2010, "A Practical Guide to High Resolution Melt Analysis Genotyping", tech note 6004.
Wittwer, et al., 2003, High-Resolution Genotyping by Amplicon Melting Analysis Using LCGreen, Clinical Chemistry, 49(6):853-860.
Vossen et al., 2009, "High-Resolution Melting Analysis (HRMA)—More Than Just Sequence Variant Screening", Hum Mutat, 30:860-868.
Corbett, 2006, "High Resolution Melt Assay Design and Analysis".
Taylor, et al., 2009, "Mutation Scanning Using High-Resolution Melting", Biochem Soc Trans, 37:433-437.
Applied Biosystems, 2010, "A Guide to High Resolution Melting (HRM) Analysis".
BIO-RAD (hereinafter BIO-RAD2), 2010, "Gradient optimization of a highresolution melt (HRM) assay for targeted cancer therapy screening using SsoFast(TM) EvaGreen(R) supermix and the CFX96(TM) real-time PCR detection system", BioTechniques Protocol Guide, p. 37.
Rozen, et al. 2000, "Primer3 on the WWW for General Users and for Biologist Programmers, in Methods in Molecular Biology", Bioinformatics Methods and Protocols, vol. 132.
Buck, et al. 1999, "Design Strategies and Performance of Custom DNA Sequencing Primers", Biotechniques, 27(3):528-535.
Lowe, et al., 1990, Nucleic Acids Research, 18(7):1757-1761.
NCBI Accesion No. EU332835 (Feb. 6, 2008).
NCBI Accesion No. GM011233 (Dec. 14, 2008).
NCBI Accesion No. BD495635 (Nov. 4, 2005).
NCBI Accesion No. X01669 (Jul. 6, 1989).
NCBI Accesion No. CS374030 (Aug. 22, 2006).
NCBI Accesion No. GN338008 (Apr. 27, 2009).
NCBI Accesion No. FB665457 (Nov. 1, 2008).
Amado, Rafael G., et al, 2008, "Wild-Type KRAS is Required for Panitumumab Efficacy in Patients With Metastatic Colorectal Cancer", American Society of Clinical Oncology, 26(10):1626-1634.
Amicarelli, Giulia, et al., 2007, "FLAG assay as a novel method for real-time signal generation during PCR: application to detection and genotyping of KRAS code 12 mutations", Nucleic Acids Res. 35(19):e131.
Angulo, Barbara, et al., 2010, "A Commercial Real-Time PCR Kit Provides Greater Sensitivity than Direct Sequencing to Detect KRAS Mutations", Journal of Molecular Diagnostics, 12(3):292-299.
Baselga, J., 2001, "The EGFR as a target for anticancer therapy-focus on cetuximab", European Journal of Cancer, 37:S16-S22.
Binladen, Jonas, et al., 2007, "The Use of Coded PCR Primers Enables High-Throughput Sequencing of Multiple Homolog Amplification Products by 454 Parallel Sequencing", PLoS ONE, 2:E197. 1-E197.9.
Bollag, Gideon, et al., 2010, "Clinical efficacy of a RAF inhibitor needs broad target blockade in BRAF-mutant melanoma", Nature, 467:596-599.
Cunningham, David, et al., 2004, "Cetuximab Monotherapy and cetuximab Plus Irinotecan in Irinotecan-Refractory metastatic Colorectal Cancer", The New England Journal of Medicine, 351:337-345.
Curtin, John A., et al., 2005, "Distinct Sets of Genetic Alterations in Melanoma", The New England Journal of Medicine, 353:2135-2147.
Di Fiore, F., 2007, "Clinical relevance of KRAS mutation detection in metastatic colorectal cancer treated by Cetuximab Plus chemotherapy", British Journal of Cancer, 96:1166-1169.
Di Nicolantonio, Federica, et al., 2008, "Wild-Type BRAF Is Required for Response to Panitumumab or Cetuximab in Metastatic Colorectal Cancer", Journal of Clinical Oncology, 26(35):5705-5712.
Dunlap, Jennifer, et al., 2010, "Phosphatidylinositol-3-Kinase and AKT1 mutations occur early in breast carcinoma", Breast Cancer Res. Treat 120:409-418.
Ferraz, Jean-Marc, et al., 2004, Impact of GSTT1, GSTM1, GSTP1 and NAT2 Genotypes on KRAS2 and TP53 Gene Mutations in Colorectal Cancer., Int J. Cancer 110:183-187.
Flaherty, Keith T., et al., 2010, "Inhibition of Mutated, Activated BRAF in Metastatic Melanoma", The New England Journal of Medicine, 363(9):809-819.
Franklin, Wilbur A., et al., 2010, "Comparison of Testing Methods and Tissue Sampling Techniques in Colon Cancer", Journal of Molecular Diagnostics, 12(1):43-50.
Herrmann, Mark G., et al., 2006, "Amplicon DNA Melting Analysis for Mutation Scanning and Genotyping: Cross-Platform Comparison of Instruments and Dyes" Clinical Chemistry, 52(3):494-503.
Krypuy, Michael, et al., 2006, "High resolution melting analysis for the rapid and sensitive detection of mutations in clinical sample: KRAS codon 12 and 13 mutations in non-small cell lung cancer", BMC Cancer, 6:295.
Lievre, Astrid, et al., 2006, "KRAS Mutation Status Is Predictive of Response to Cetuximab Therapy in Colorectal Cancer", Cancer Research, 66:3992-3995.
Ma, E. E. K., et al., 2009, "Detection of KRAS mutations in colorectal cancer by high-resolution melting analysis", Journal of Clinical Pathology, 62:886-891.
McGrath, John P., et al., 1983, "Structure and organization of the human Ki-ras Proto-oncogene and a related processed pseudogene", Nature, 304:501-506.
Monzon, Federico A., et al., 2009, "The Role of KRAS Mutation Testing in the Management of Patients With Metastatic Colorectal Cancer", Archives Pathology Laboratory Medicine, 133-1600-1606.
Muller, Claudia I., et al., 2007, "Rare mutations of the PIK3CA gene in malignancies of the hematopoietic system as well as endometrium, ovary, prostate and osteosarcomas, and discovery of a PIK3CA pseudogene", Leukemia Research, 31:27-32.
Ogino, Shuji, et al., 2005, "Sensitive Sequencing Method for KRAS Mutation Detection by Pyrosequencing". Journal of Molecular Diagnostics, 7(3):413-421.
Pichler, Martin, et al., 2009, "Evolution of High-Resolution Melting Analysis as a Diagnostic Tool to Detect the BRAF V600E Mutation in Colorectal Tumors", Journal of Molecular Diagnostics, 11(2):140-147.
Reed Gudrum H., et al., 2007, "High-resolution DNA melting analysis for simple and efficient molecular diagnostics", Pharmacogenomics, 8(6):597-608.
Rubinstein, Jill C., et al., 2010, "Incidence of the V600K mutation among melanoma patients with BRAF mutations, and potential therapeutic response to the specific BRAF inhibitor PLX4030", Journal of Translational Medicine, 8:67.
Saltz, Leonard B., et al., 2004, "Phase II Trial of Cetuximab in Patients With Refractory Colorectal Cancer That Expresses the Epidermal Growth Factor Receptor", Journal of Clinical Oncology, 22(7):1201-1208.
Schubbert, Suzanne, et al., 2006, "Germline KRAS mutations cause Noonan syndrome", Nature Genetics, 38(3):331-336.
Servomaa, K., et al., 2000, "p53 and K-ras mutations in carcinoma of the rectum among Finnish women", Molecular Pathology, 53:24-30.
Seth R., et al., 2009, "Concomitant mutations and splice variants in KRAS and BRAF demonstrate complex perturbation of the Ras/Raf signalling pathway in advanced colorectal cancer", Gut 58:1234-1241.
Sithanandam, Gunamani, et al., 1992, "B-raf and a B-ref pseudogene are located on 7q in man", Oncogene, 7:795-799.
Sos, Martin L., et al., 2009, "Identifying genotype-dependent efficacy of single and combined P13K- and MAPK-pathway inhibition in cancer", Proceeding National Academy Sciences USA, 106(43):18351-18356.
Tol, Jolien, et al., 2010, "Markers for EGFR pathway activation as predictor of outcome in metastatic colorectal cancer patients treated with or without cetuximab", European Journal of Cancer, 46:1997-2009.

(56) References Cited

OTHER PUBLICATIONS

Tyner, Jeffrey W., et al., 2009, "High-throughput sequencing screen reveals novel, transforming RAS mutations in myeloid leukemia patients", Blood, 113:1749-1755.

Van Cutsem, Eric, et al., 2007, "Open-Label Phase III Trial of Panitumumab Plus Best Supportive Care Compared With Best Supportive Care Alone in Patients With Chemotherapy-Refractory Metastatic Colorectal Cancer", Journal of Clinical Oncology, 25(13):1658-1664.

Van Eijk, Ronald, et al., 2010, "Sensitive and Specific KRAS Somatic Mutation Analysis on Whole-Genome Amplified DNA from Archival Tissues", Journal of Molecular Diagnostics, 12(1):27-34.

Vorkas, Panagiotis, et al., 2010, "Mutation scanning of exon 20 of the BRCA1 gene by high-resolution melting curve analysis", Clinical Biochemistry, 43:178-185.

Yunxia, Zuo, et al., 2010, "Mutations in epidermal growth factor receptor and K-ras in Chinese patients with colorectal cancer", BMC Medical Genetics, 11:34.

Zhou, Luming, et al., 2005, "High-Resolution DNA Melting Analysis for Simultaneous Mutation Scanning and Genotyping in Solution", Clinical Chemistry, 51(10):1770-1777.

Database Geneseq [Online] Sep. 16, 2010 (Sep. 16, 2010), "KRAS gene to MGB blocker 1 (MGB1) sequence #8.", retrieved from EBI accession No. GSN:AYE57158Database accession No. AYE57158.

Database Geneseq [Online] Sep. 2, 2010 (Sep. 2, 2010), "KRAS gene fragment specific MGB blocker 1 (MGB1) probe #9.",retrieved from EBI accession No. GSN:AYE51496Database accession No. AYE51496.

Deschoolmeester V. et al., KRAS mutation defection and prognostic potential in spoadic colorectal cancer using high-resolution melting analysis, British Journal of Cancer, Nov. 9, 2010, pp. 1627-1636, vol. 103, No. 10, Cancer Research UK.

Do H. et al., High resolution melting analysis for rapid and sensitive EGFR and KRAS mutation detection in formalin fixed paraffin embedded biopsies, BMC Cancer, May 21, 2008, p. 142 (1-14), vol. 8, No. 1, BioMed Central Ltd.

Krypuy M. et al., High resolution melting analysis for the rapid and sensitive detection of mutations in clinical samples: KRAS codon 12 and 13 mutations in non-small cell lung cancer, BMC Cancer, Dec. 21, 2006, p. 295 (1-12), vol. 6, BioMed Central Ltd.

Ma E.S.K. et al., Detection of KRAS mutations in colorectal cancer by high-resolution melting analysis, Journal of Clinical Pathology, Jan. 1, 2009, pp. 869-891, vol. 62, No. 10, BMJ.

Office Action Art. 94(3) EPC dated Mar. 15, 2016 in Application No. EP12701076.3, 10 pages.

Simi L. et al., High-Resolution Melting Analysis for Rapid Detection of KRAS, BRAF, and PIK3CA Gene Mutations in Colorectal Cancer, American Journal of Clinical Pathology, Aug. 2008, pp. 247-253, vol. 130, No. 2, American Society for Clinical Pathology.

Vorkas, Panagiotis A. et al., PIK3CA Hotpot Mutation Scanning by a Novel and Highly Sensitive High-Resolution Small Amplicon Melting Analysis Method, Journal of Molecular Diagnostics, Sep. 1, 2010, pp. 697-704, vol. 12, No. 5, American Society for Investigative Pathology.

\* cited by examiner

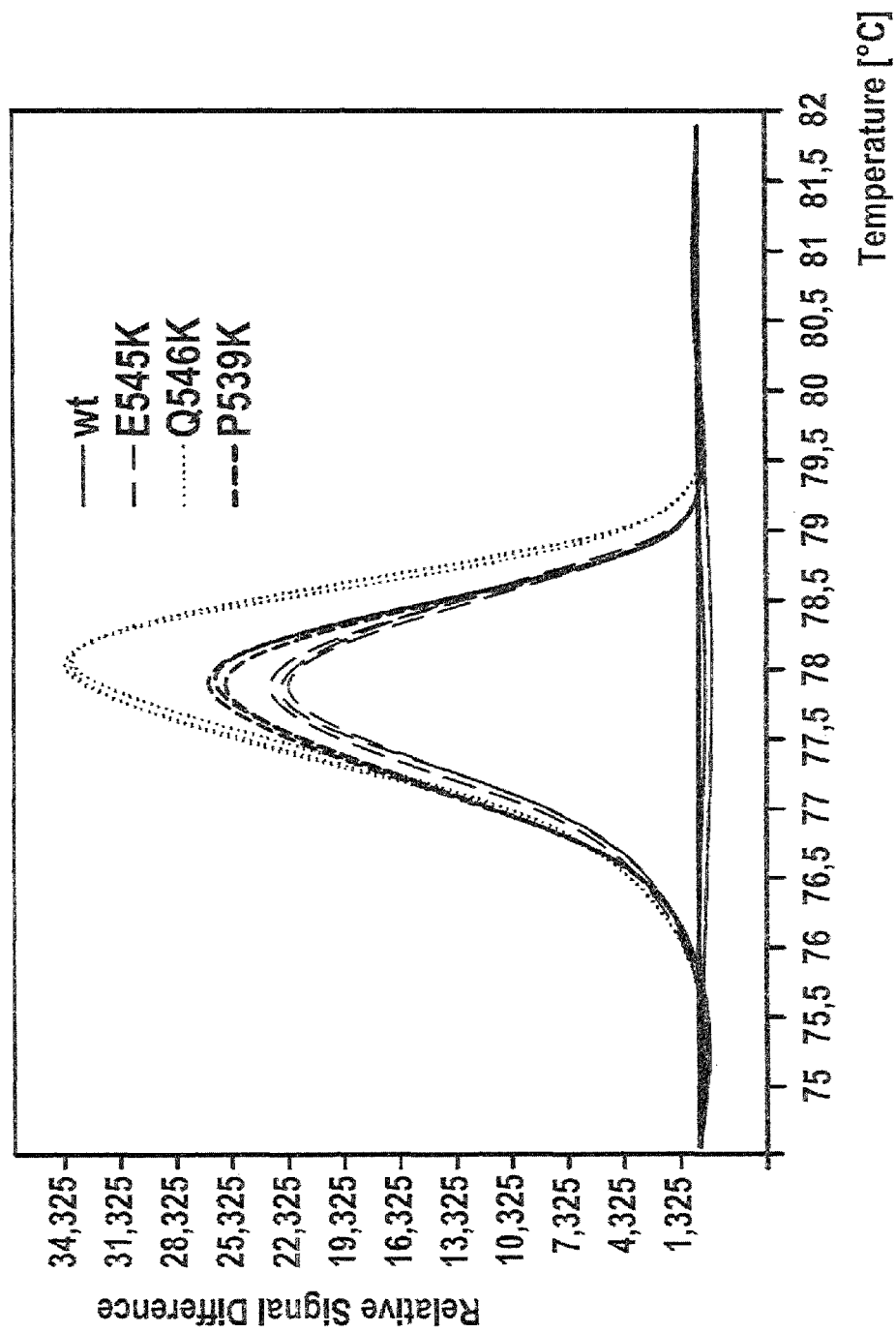

HIGH RESOLUTION MELTING ANALYSIS AS A PRESCREENING TOOL

CROSS-REFERENCE TO RELATED APPLICATIONS

This application is a divisional of U.S. Ser. No. 14/615,877, filed Feb. 6, 2015, which is a continuation of U.S. Ser. No. 13/930,638 filed on Jun. 28, 2013, now U.S. Pat. No. 8,980,556, which is a continuation of International Application No. PCT/EP2012/050213, filed Jan. 9, 2012, which claims the benefit of European Patent Application No. 11150641.6, filed Jan. 11, 2011, the disclosures of which are hereby incorporated by reference in their entireties.

SEQUENCE LISTING

The instant application contains a Sequence Listing which has been submitted in ASCII format via EFS-Web and is hereby incorporated by reference in its entirety. Said ASCII copy, created on Jun. 27, 2013, is named SEQUENCE_LISTING_27206US.txt, and is six thousand nine hundred and ninety-five bytes in size.

BACKGROUND OF THE DISCLOSURE

Therapeutic agents targeting molecular changes are involved in the treatment of several human cancers. The epidermal growth factor receptor (EGFR), a transmembrane tyrosine kinase receptor, is one of the targets in colorectal cancer therapy because of its deregulation in 60% to 80% of the cases. Activated signaling pathways include the RAS/RAF/mitogen-activated protein kinase (MAPK) pathway and the phosphatidylinositol3-kinase (PI3K)/PTEN/AKT pathway involved in cell proliferation, angiogenesis, apoptosis and metastatic processes (Baselga, J., Eur. J. Cancer 37 Suppl 4 (2001) S16-S22).

Monoclonal antibodies targeting EGFR, like cetuximab (Erbitux®) and panitumumab (Vectibix®) have entered clinical practice and have shown benefit in approximately 10% to 20% of patients with colorectal cancers due to the inhibition of downstream pathways (Amado, R. G., et al., J. Clin. Oncol. 26 (2008) 1626-1634; Cunningham, D., et al., N. Engl. J. Med. 351 (2004) 337-345; Saltz, L. B., et al., J. Clin Oncol. 22 (2004) 1201-1208; Van Cutsem, E., et al., J. Clin. Oncol. 25 (2007) 1658-1664). Previous work has shown that mutations in KRAS negatively correlate with the response to anti-EGFR antibodies and therefore are an independent predictive marker of resistance against this therapy (Lievre, A., et al., Cancer Res. 66 (2006) 3992-3995). Based on these results, the European Medicines Agency (EMEA), has approved the use of panitumumab and cetuximab only for patients with metastatic colorectal cancer without activating mutations in KRAS and mutation analyses should be part of the pretreatment. KRAS mutations account for 30% to 40% of the cases resistant to anti-EGFR therapies (Di Fiore, F., et al., Br. J. Cancer 96 (2007) 1166-1169; Lievre, A., et al., Cancer Res. 66 (2006) 3992-3995). Some studies suggested that additional mutations concerning the RAS/RAF/MAPK and PI3K/PTEN/AKT pathway are involved. Patients with wildtype KRAS and mutations in BRAF do not respond to anti-EGFR therapy, whereas wildtype BRAF status seemed to increase the therapy efficiency (Di Nicolantonio. F., at al., J. Clin. Oncol. 26 (2008) 5705-5712). Recently it was shown that BRAF mutations in colorectal cancer are rather of prognostic than predictive value (Tol, J., et al., Eur. J. Cancer 46 (2010) 1997-2009).

The BRAF V600E mutation is ore of the most common mutations in human cancer with a high incidence in malignant melanoma (Curtin, J. A., et al., N. Engl. J. Med. 353 (2005) 2135-2147). High objective response rates in melanoma patients carrying this mutation were observed in the phase I clinical trial of the RAF inhibitor PLX4032 and phase II and phase III studies are limited to patients with BRAF V600E mutation (Flaherty, K. T., et al., N. Engl. J. Med. 363 (2010) 809-819). Recently it has been shown that patient bearing the BRAF V600K mutation respond remarkably to PLX4032, suggesting that mutation assays for codon 600 should at least include the exchanges V600E and V600K (Bollag, G., et al., Nature 467 (2010) 596-599; Rubinstein, J. C., et al., J. Transl. Med. 8 (2010) 67).

PIK3CA mutations have been described in up to 40% of invasive breast carcinoma, and AKT1 mutations have been found in up to 8% of breast carcinoma (Dunlap, J., et al., Breast Cancer Res. Treat 120 (2010) 409-418). These mutations occur early in breast cancer development and may have implications on the selection of therapeutics targeting the PI3 kinase pathway. Moreover it has been shown in lung cancer that combined inhibition of activated PI3K and MAPK signaling might be clinically beneficial (Sos, M. L., at al., Proc. Natl. Acad. Sci. USA 106 (2009) 18351-18358).

BRIEF SUMMARY OF THE DISCLOSURE

The present disclosure relates to the field of predicting susceptibility for certain tumor therapies by means of appropriate mutational analysis of the patient's genome. Embodiments of the instant application disclose High Resolution Melting (HRM) assays as a prescreening diagnostic method to diagnose mutations in the hot spot regions of the most common genes (KRAS, BRAF, PIK3CA, AKT1) concerning the RAS/RAF/MAPK and PI3K/PTEN/AKT pathway.

According to some embodiments, the present disclosure provides pairs of amplification primers, which are useful for HRM analysis of genes which are important for predicting responsiveness to cancer therapeutic agents. In particular, the present disclosure provides the following pairs of amplification primers for amplification and analysis of KRAS, exons 2 and 3, BRAF, exon 15, PIK3CA, exons 7, 9 and 20, and AKT1, exon 2. More precisely, the present disclosure provides the following primer pairs:

Seq. ID. No: 1 and Seq. ID. NO: 2 AKT 1, exon 2
Seq. ID. No: 3 and Seq. ID. NO: 4 AKT1, exon 2
Seq. ID. No: 5 and Seq. ID. NO: 6 BRAF, exon 15
Seq. ID. No: 7 and Seq. ID. NO: 8 BRAF, exon 15
Seq. ID. No: 9 and Seq. ID. NO: 10 KRAS, exon 2
Seq. ID. No: 11 and Seq. ID. NO: 12 KRAS, exon 2
Seq. ID. No: 13 and Seq. ID. NO: 14 KRAS, exon 3
Seq. ID. No: 15 and Seq. ID. NO: 16 KRAS, exon 3
Seq. ID. No: 17 and Seq. ID. NO: 18 PIK3CA, exon 7
Seq. ID. No: 19 and Seq. ID. NO: 20 PIK3CA, exon 7
Seq. ID. No: 21 and Seq. ID. NO: 22 PIK3CA, exon 9
Seq. ID. No: 23 and Seq. ID. NO: 24 PIK3CA, exon 9
Seq. ID. No: 25 and Seq. ID. NO: 26 PIK3CA, exon 20
Seq. ID. No: 27 and Seq. ID. NO: 28 PIK3CA, exon 20

Embodiments of the present disclosure also provide a composition or reaction mixture comprising at least one pair of amplification primers as disclosed above. The composition may be used for PCR amplification of nucleic acids during a nucleic acid amplification reaction, and also PCR amplification and monitoring in real time. According to some embodiments of the present disclosure, a mixture comprises at least: a pair of amplification primers as disclosed above; a thermostable DNA Polymerase; a mix of deoxynucleoside triphosphates which is usually dA, dG, dC and dT, or dA, dG, dC and dU; and a buffer.

In some further embodiments, when suitable for amplification and detection in real time, of one or more specific nucleic acid target sequence(s) such a composition additionally comprises a nucleic acid detecting entity such as a fluorescent hybridization probe, or a fluorescent, double stranded DNA binding dye. In some embodiments, such a DNA double stranded Dye is a dye which can be used to perform HRM curve analysis. Illustrative embodiments of such dye include the LightCycler® 480 Resolight dye (Roche Applied Science Cat. No: 04 909 640 001) or similar compounds as disclosed in WO 2008/052742.

According to some illustrative embodiments of the instant disclosure, the pair of amplification primers is designed to amplify a specific sequence of interest according to standard methods known in the art of molecular biology. In some embodiments, when brought into contact with a sample that shall be analyzed, such a PCR reaction mixture additionally comprises an at least partially purified DNA or other nucleic acid which putatively comprises a specific sequence of interest. Also, in some such embodiments, the concentrations of all reagents included are generally as known to persons skilled in the art and can be optimized for specific adaptations according to standard protocols. In some such embodiments, the concentration of the fluorescent, double stranded DNA binding dye is between approximately 0.1 to 10.0 µg/ml.

In some embodiments of the instant disclosure, a kit is provided. Some illustrative embodiments of kits disclosed herein include at least one pair of amplification primers as disclosed above and herein. Some embodiments of kits disclosed herein may further comprise one, several, or all of the following additional ingredients; a thermostable DNA Polymerase; a mix of deoxynucleoside triphosphates which is usually dA, dG, dC and dT, or dA, dG, dC and dU, and a buffer, and a fluorescent, double stranded DNA binding dye, which may be suited to be used for HRM.

In yet additional embodiments of the instant disclosure, oligonucleotides are provided which may be used as hybridization probes for new nucleotide sequence variations with KRAS, for example which haven't been disclosed in the art. In some such embodiments, the present disclosure also provides an oligonucleotide comprising a sequence selected from a group consisting of Seq. ID. NO: 31 or its complement, Seq. ID. NO: 32 or its complement, Seq. ID. NO: 33 or its complement, and Seq. ID. NO: 34 or its complement.

In even further embodiments, the present disclosure is directed to a method for determining the increased likelihood of a response to a targeted treatment of a cancer disease, comprising the steps of:
  a) isolating genomic DNA from a patient sample;
  b) amplifying at least one fragment of said DNA by means of PCR with a specific pair of amplification primers;
  c) determining, whether said amplified fragment has a wildtype sequence or comprises a mutation by means of a High Resolution Melting Analysis (HRM); and
  d) correlating the presence or absence of a mutation with an increased likelihood of success of said targeted treatment.

According to some embodiments, the mutation is identified by means of a hybridization analysis or by means of sequencing. For example, the patient sample may be Formalin Fixed Paraffin Embedded (FFPE) tissue. In some such cases, HRM Analysis may be performed without any spiking of DNA.

In some even further embodiments, the (at least one) fragment is selected from a group comprising KRAS, exon 2, KRAS, Exon 3, BRAF exon 15, PIK3CA exon 7, PIK3CA exon 9, PIK3CA exon 20, and AKT1 exon 2. In some such embodiments, at least one pair of amplification primers selected from the group consisting of: Seq. ID. No: 1 and Seq. ID. NO: 2; Seq. ID. No: 3 and Seq. ID. NO: 4; Seq. ID. No: 5 and Seq. ID. NO: 6; Seq. ID. No: 7 and Seq. ID. NO: 8; Seq. ID. No: 9 and Seq. ID. NO: 10; Seq. ID. No: 11 and Seq. ID. NO: 12; Seq. ID. No: 13 and Seq. ID. NO: 14; Seq. ID. No: 15 and Seq. ID. NO: 16; Seq. ID. No: 17 and Seq. ID. NO: 18; Seq. ID. No: 19 and Seq. ID. NO: 20; Seq. ID. No: 21 and Seq. ID. NO: 22; Seq. ID. No: 23 and Seq. ID. NO: 24; Seq. ID. No: 25 and Seq. ID. NO: 26; and Seq. ID. No: 27 and Seq. ID. NO: 28, is used.

BRIEF DESCRIPTION OF THE FIGURES

The features of this disclosure, and the manner of attaining them, will become more apparent and the disclosure itself will be better understood by reference to the following description of embodiments of the disclosure taken in conjunction with the accompanying drawing.

FIG. 1A-1F show a comparison of KRAS exon 2 (A-C) and PIK3CA exon 9 (D-F) HRM assays using DNA isolated from cell lines (A and D) or from FFPE tissues (B and E). All samples are displayed in triplicates. (A), (B):KRAS wildtype: HT-29, KRAS mutations: HCT116 (G13D, heterozygous), LoVo (G12V, homozygous), A549 (G12S, homozygous), RPMI 8226 (G12A, heterozygous), LS174T (G12D, heterozygous), Mia PaCa-2 (G12C, homozygous); and (D), (E): PIK3CA wildtype: HCT116, P/K3CA mutations: MCF-7 (E545K, heterozygous), NCI N417 (Q546K, heterozygous) and BT-20 (P539K, heterozygous); (C), (F): Determination of the sensitivities of KRAS exon 2 (C) and PIK3CA exon 9 (F) HRM mutations assays. Percentages indicate the proportion of mutant DNA relative to wildtype DNA. 6.3% (C) and 3.1% (F) of mutated DNA isolated from HCT116 (G13D, heterozygous, C) or NCI N417 (Q546K, heterozygous, F) were detectable.

Figure 1A:
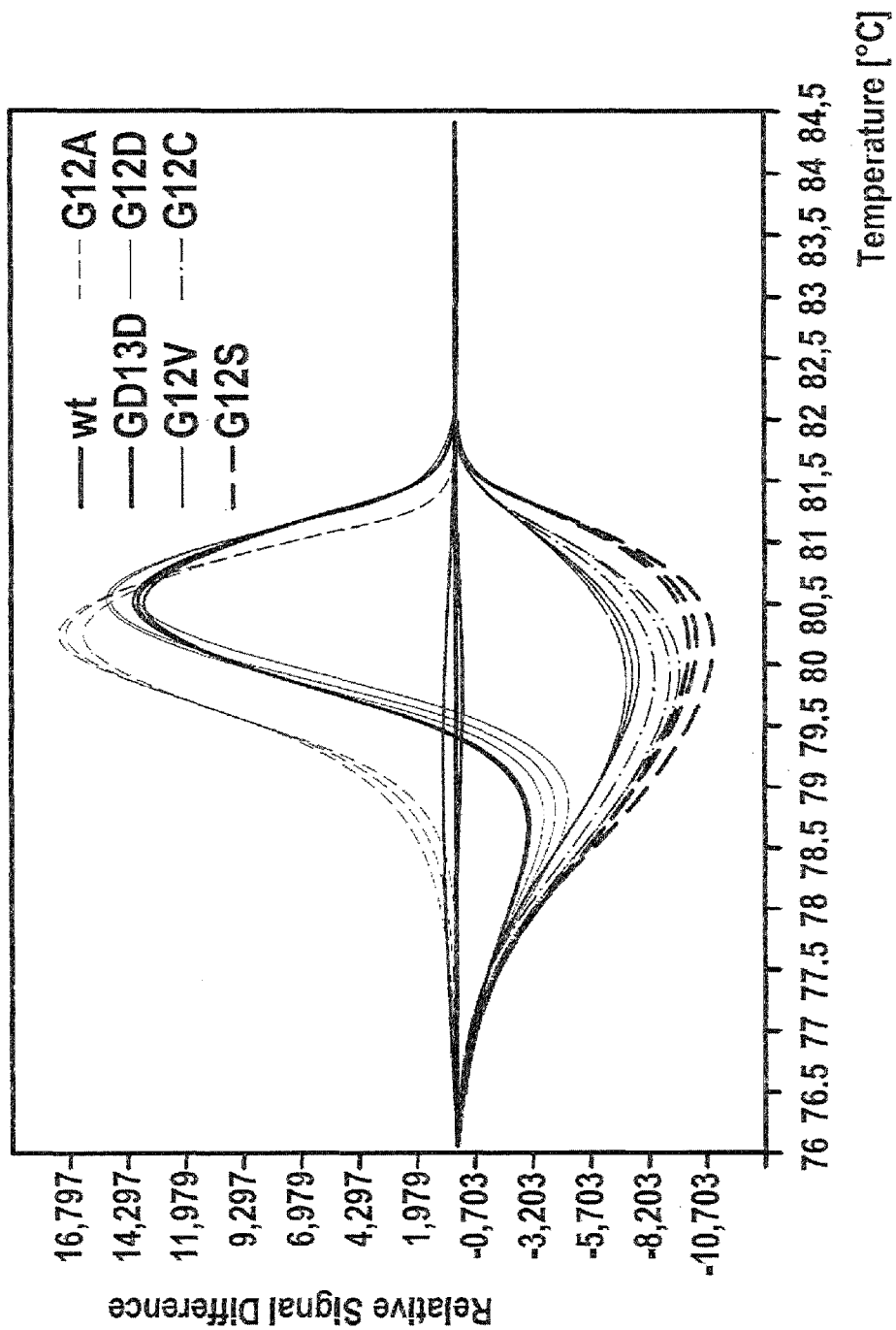

Corresponding reference characters indicate corresponding parts throughout the several views. Although the drawings represent embodiments of the present disclosure, the drawings are not necessarily to scale and certain features may be exaggerated in order to better illustrate and explain the present disclosure. The exemplifications set out herein illustrate an exemplary embodiment of the disclosure, in one form, and such exemplifications are not to be construed as limiting the scope of the disclosure in any manner.

DETAILED DESCRIPTION OF THE DISCLOSURE

The embodiments disclosed herein are not intended to be exhaustive or limit the disclosure to the precise form disclosed in the following detailed description. Rather, the embodiments are chosen and described so that others skilled in the art may utilize their teachings.

Target specific therapies require specific and sensitive mutation screening methods, which allow fast and high throughput analyses. Various methods have been described for the detection of mutations, such as Sanger Sequencing (Yunxia, Z., et al., BMC Med. Genet. 11 (2010) 34), real-time PCR (Amicarelli, G., et al., Nucleic. Acids Res. 35 (2007) e131) and pyrosequencing (Ogino, S., et al., J. Mol. Diagn. 7 (2005) 413-421).

Recently, High Resolution Melting (HRM) was introduced ed as a new molecular technique for high throughput mutation scanning (Zhou, L., et al., Clin. Chem. 51 (2005) 1770-1777). For example, HRM instrumentation (Roche Applied science Cat. No: 05 015 278 001), software ((Roche Applied Science Cat. No: 05 103 908 001) and dyes (Roche Applied Science Cat. No: 04 909 640 001) are commercially available. Mutation determination using HRM is based on the dissociation of DNA, when exposed to an increasing temperature in the presence of fluorescent dyes interacting with double-stranded DNA (see, for example U.S. Pat. No. 7,387,887, U.S. Pat. No. 7,582,429). There are numerous appropriate dyes disclosed in the art. The presence of a mutation leads to the formation of DNA heteroduplexes followed by a change in melting behaviour.

High Resolution Melting (HRM) is a mutation scanning" technique that detects the presence of sequence variations in target-gene derived PCR amplicons. HRM enables genomic researchers to analyze genetic variations in PCR amplicons prior to or as alternative to sequencing by means of a closed-tube post-PCR (Polymerase Chain Reaction) analysis method. High Resolution Melting provides high specificity, sensitivity and convenience at significantly higher speed and lower cost than other established (e.g., gel-based) methods. For example, in a diploid genome, equivalent regions from maternal and paternal chromosomes are both amplified by the Polymerase Chain Reaction. The PCR products can then be analyzed for completely matched hybrids (called homoduplexes) and mismatched hybrids (heteroduplexes). Thus, the entire mutation screening process is homogeneous. High Resolution Melting, is a refinement of earlier, well-established DNA dissociation (or "melting") techniques (e.g., to determine the Tm of a DNA hybrid). Like all melting analyses, the technique subjects DNA samples to increasing temperatures and records the details of their dissociation from double-stranded (dsDNA) to single-stranded form (ssDNA).

Before a High Resolution Melting analysis can be performed, the target sequence must be available in high copy number. The easiest way to accomplish this is to perform a DNA amplification reaction (PCR) in the presence of a High Resolution Melting Dye before the High Resolution Melt. Prominent examples of such dyes are disclosed in WO 2008/052742. After PCR, the successive melting experiment can be performed on the same Real Time Instrument, and analyzed with a respective Gene Scanning Software to identify sequence variants. As such, the entire experiment can be done without opening the reaction vessels and without additional handling steps after the PCR setup. Both procedures are performed in the presence of a fluorescent dye that binds only dsDNA. The dye does not interact with ssDNA, but fluoresces strongly in the presence of dsDNA. This change in fluorescence can be used both to measure the increase in DNA concentration during PCR and then to directly measure thermally-induced DNA dissociation during High Resolution Melting.

For detection of sequence variations, differences in the melting curves of the amplicons are analyzed. Heterozygote DNA forms heteroduplices that begin to separate into single strands at a lower temperature and with a different curve shape than homozygote DNA. Depending on the individual sequence, most of the different homozygotes give distinguishable melting curves, too.

In a melting experiment, fluorescence is initially high because the sample starts as dsDNA, but fluorescence diminishes as the temperature is raised and DNA dissociates into single strands. The observed "melting" behavior is characteristic of a particular DNA sample. Mutations in PCR products are detectable because they change the shape of the melting curve. When the mutant sample is compared to a reference "wild type" sample, these changes are visible.

Usually, an analysis of HRM data is supported by a respective software, which, in some embodiments, advantageously provides for the following analysis steps:

Normalization: The raw melting curve data can be normalized by setting the pre-melt (initial fluorescence) and post-melt (final fluorescence) signals of all samples to uniform values. Pre-melt signals are uniformly set to a relative value of 100%, while post-melt signals are set to a relative value of 0%. Normalizing the initial and final fluorescence in all samples aids interpretation and analysis of the data. In some cases, samples with homozygous SNPs may be distinguished from the wild type by the displacement of their melting curves, which is easier to see in the normalized data.

Temperature shifting: A shift on the temperature axis of the normalized melting curves at the point where the entire double-stranded DNA is completely denatured.

Difference Plot: Further information on the differences in melting curve shapes, different can be obtained by means of subtracting the curves from a reference curve (also called "base curve"), thus generating a Difference Plot, which helps duster samples automatically into groups that have similar melting curves.

Summarizing, High Resolution Melting (HRM) can be defined as a method comprising the steps of: monitoring temperature dependent fluorescence of the dsDNA binding dye in order to generate a melting curve from a previously amplified target nucleic acid; repeating the providing, amplifying, monitoring and generating steps with at least one additional previously amplified target nucleic acid, and comparing the generated melting curves with each other.

Such a comparison may be achieved by means of creating a Difference Plot. For example, amplification may be performed by means of PCR, during which said dsDNA binding dye is already present within the sample such that the whole assays can be performed in a homogenous manner.

As the availability for targeted therapies for several tumor types increases the need for rapid and sensitive mutation screening is growing. The aim of the inventors was to establish High Resolution Melting (HRM) assays for routinely used predictive analyses of KRAS, AKT1, PIK3CA and BRAF mutations. In KRAS mutations constitutively activate the RAS/RAF/mitogen-activated protein kinase (MAPK) pathway and therefore play an important role in anti-EGFR therapy for patients with colorectal cancers. Mutationally activated PIK3CA and AKT1 are promising therapeutic targets in breast cancer. In 60-70% of malignant melanoma a mutation in BRAF can be found. Thus blocking the oncogenic signalling induced by this mutation is employed now as treatment approach.

HRM assays were developed using genomic DNA containing the desired mutation, enabling the detection of 3.1% to 12.5% mutated DNA mixed in wildtype background. For KRAS (exon 2) and PIK3CA (exon 9), assays were proofed by hybridization probes and/or Sanger Sequencing to exclude pseudogene amplification. The HRM assays were validated using genomic DNA isolated from formalin-fixed paraffin-embedded (FFPE) tissues from different tumor entities. Sanger Sequencing was used to confirm and characterize HRM results. The concordance between Sanger Sequencing and HRM was 99% for KRAS exon 2 and PIK3CA exon 20 and 100% for the remaining assays. In conclusion HRM provides a powerful tool to detect genomic mutations efficiently.

High sensitivity, high specificity, transferability to other tumor entities and robustness in analysing low-quality genomic DNA isolated from FFPE tissues, were highly important prerequisites for the development of new HRM mutation assays. As such, HRM assays were established and optimized using DNA samples bearing the most frequent mutations in the genes of interest. For each at least three different primer sets were tested in order to find optimal conditions. The sensitivity of each assay was assessed by testing dilutions of mutated DNA strands in a wildtype background. Special attention was paid to the exclusion of pseudogene amplification. Finally all HRM assays were validated using a collection of FFPE tissues from various tumor entities. Mutation analyses from all FFPE tissues were additionally confirmed by Sanger Sequencing.

The development of targeted therapies and therefore the identification of predictive markers is gaining importance in the field of molecular diagnostics. Determination of genetic markers in several tumor entities allows individualized treatment of patients, as for example the KRAS mutation analysis which helps to predict the response to anti-EGFR therapy in patients with colorectal cancer (Amado, R. G., et al., J. Clin. Oncol. 26 (2008) 1626-1634; Lievre, A., et al., Cancer Res. 66 (2006) 3992-3995).

The present disclosure provides high sensitive testing methods that allow rapid identification of hot-spot mutations in the main genes (KRAS, BRAF, PIK3CA, AKT1) involved in the RAS/RAF/MAPK and PI3K/PTEN/AKT pathway.

The present disclosure discloses the use of HRM analysis as a reliable and sensitive prescreening technology to detect genomic changes in DNA isolated from FFPE tissues. Several methods used in the art to determine genomic variations are described, for example Sanger Sequencing, the gold standard for mutational analysis, pyrosequencing or real-time-based PCR analysis. The major disadvantage for real-time-based PCR analyses is the need for expensive fluorescence-labeled probes. Pyrosequencing provides a sensitive method, but may not be economical due to expensive equipment (Pichler, M., et al., J. Mol. Diagn. 11 (2009) 140-147). Compared to that HRM is a cost effective method, which is at the same time fast in contrast to Sanger Sequencing (Franklin, W. A., et al., J. Mol. Diagn. 12 (2010) 43-50; Monzon, F. A., et al., Arch. Pathol. Lab. Med. 133 (2009) 1600-1606). HRM is highly applicable for large scale genotyping because of its sensitivity and simplicity as well as the low DNA amount required. It can be used as a prescreening method and followed by direct Sanger Sequencing of the HRM product when additional determination of the exact mutation is needed. This saves manpower and resources and provides rapid results concerning all patients without mutations.

HRM analysis allows the detection of a wide spectrum of mutations whereas the commercially available TheraScreen K-RAS Kit is only able to detect seven mutations in KRAS exon 2 (G12D, G12V, G12C, G12S, G12A, G12R, G13D) targeted by the designed primers within the kit. In the case of untargeted mutation the kit provides a false negative result (Angulo, B., et al., J. Mol. Diagn. 12 (2010) 292-299). Additionally to the seven main KRAS mutations, three mutations (G13C, G13_V14insG, V14A) could be detected using the HRM assay which are not included in the TheraScreen K-RAS Kit. An insertion mutation of KRAS codon 12 (G12_G13insG) is already published (Servomaa, K., et al., Mol. Pathol. 53 (2000) 24-30). The inventors have identified an insertion mutation of KRAS codon 13 (G13_V14insG) and a point mutation (V14A) which are both to the best of their knowledge not described yet. However KRAS V14I mutations are described in colorectal cancer (Ferraz, J. M., et al., Int. J. Cancer 110 (2004) 183-187), myeloid leukemia (Tyner, J. W., et al., Blood 113 (2009) 1749-1755) and in three patients with Noonan syndrome (Schubbert, S., et al., Nat. Genet. 38 (2006) 331-336). Functional assays exhibited oncogenic properties of V14I mutation in comparison to wildtype KRAS (Tyner, J. W., et al., Blood 113 (2009) 1749-1755). Concerning KRAS exon 3 HRM assay two new mutations (G60D, Q61L: c.182_183AA>TG), which are not described until now could be found. Altogether this emphasizes the necessity to use a method, which allows the detection of all genomic variations.

The sensitivities of developed HRM assays to detect genomic mutated DNA in wildtype background range from 3.1% to 12.5% and are comparable to sensitivity data described recently (Krypuy, M., et al., BMC Cancer 6 (2006) 295) and similar to alternative methods like pyrosequencing (5% to 10% (Monzon, F. A., et al., Arch. Pathol. Lab. Med. 133 (2009) 1600-1606)) or TheraScreen K-RAS Mutation Kit (5% (Angulo, B., et al., J. Mol. Diagn. 12 (2010) 292-299)). Sanger Sequencing needs a larger amplicon size (about 250 bp) compared to HRM, resulting in a higher failure rate due to the low quality of DNA isolated from FFPE tissue. Furthermore Sanger Sequencing shows a lower sensitivity of about 20-30% mutated DNA mixed with wildtype DNA (Monzon, F. A., et al., Arch. Pathol. Lab. Med. 133 (2009) 1600-1606; Pichler, M., et al., J. Mol. Diagn. 11 (2009) 140-147). Mutations found by HRM during the study underlying the present disclosure in the PIK3CA gene from three FFPE samples (3/16) could only be confirmed by Sanger Sequencing using the HRM PCR products directly and not the standard approach. This increase in sensitivity may be due to the shorter amplicon size. Using the HRM PCR product for Sanger Sequencing is not always possible. One example is KRAS exon 3 where the forward primer is located too near to the region of interest. The concordance between results from Sanger Sequencing and HRM analyses was 100% except for KRAS exon 2 and PIK3CA exon 20, which have 99% correlation. This could be due to the lower sensitivity of the Sanger Sequencing and was comparable to recent publications (95% (Ma, E. S., et al., J. Clin. Pathol. 62 (2009) 886-891), 100% (Pichler, M., et al., J. Mol. Diagn. 11 (2009) 140-147)). HRM represents a suitable method for screening of low frequency mutations such as AKT1 exon 2 or PIK3CA exon 7 mutations in clinical samples.

Referring to recent publications, the amplicon size (the shorter the better), exclusion of primer dimers, salt concentration, specific melting products with only one single melting domain and standardized geromic DNA isolation protocols are important for implementation of highly sensitive HRM assays (Pichler, M., et al., J. Mol. Diagn. 11 (2009) 140-147; Reed, G. H., et al., Pharmacogenomics 8 (2007) 597-608; van Eijk, R., et al., J. Mol. Diagn. 12 (2010) 27-34). Performing triplicates is necessary to minimize temperature differences on the microtiter plate (Herrmann, M. G., et al., Clin. Chem. 52 (2006) 494-503). By using highly sensitive hybridization probes and/or Sanger Sequencing to exclude KRAS or PIK3CA pseudogene amplification high specificity of the established HRM assays could be confirmed. Short amplicon sizes (100 bp to 183 bp)

allow analyses of low quality DNA isolated from FFPE tissues and feasibility in routine diagnostic laboratory is guaranteed.

HRM analysis detects changes it DNA melting behaviour depending on the formation of DNA heteroduplexes in the presence of a mutation. So homozygous mutations may be missed if only homoduplexes with the same melting point as the wildtype homoduplexes are generated. Therefore cell lines, plasmids or oligonucleotides were spiked with wildtype DNA to allow formation of heteroduplexes. According to the present disclosure, it is not necessary to spike wildtype DNA in FFPE samples because of the presence of non-mutated stromal cells. Several homozygous mutations comprising KRAS exon 2 G12S, G12V and G12C and the BRAF V600E mutation can be discriminated from wildtype using HRM without spiking, whereas KRAS G12R, A59E, Q61H, Q61L and E63K as well as the PIK3CA mutation E542K can only be found in the heterozygous form.

As disclosed herein, seven different HRM assays covering the hot spot regions in four different genes (KRAS, BRAF, PIK3CA and AKT1) were developed as highly specific and sensitive diagnostic tools. The validation with FFPE tissues from different tumor entities showed accurate mutation detection compared to Sanger Sequencing with a higher sensitivity for HRM analysis. HRM, as a low-cost and fast method for prescreening of genomic variations represents an alternative to established mutation detection techniques and is therefore, as shown herein, applicable for research as well as for clinical diagnostic approaches.

For the study underlying the present disclosure, seven different HRM assays (Table 1) have been developed as a prescreening diagnostic tool:

TABLE 1

List of the developed HRM Assays

| Gene | exon | codons |
|---|---|---|
| KRAS | 2 | 12, 13 |
| KRAS | 3 | 59, 61, 63 |
| BRAF | 15 | 594, 600, 601 |
| PIK3CA | 7 | 420 |
| PIK3CA | 9 | 539, 542, 545, 546 |
| PIK3CA | 20 | 1043, 1047, 1049 |
| AKT1 | 2 | 17 |

As disclosed in the Example, genomic DNA isolated from cell lines, plasmids or oligonucleotides with known mutational status were used. Several rare mutations concerning KRAS exon 3 were amplified from human FFPE tissues and cloned into the pCR-4 vector to ensure enough amount of mutated DNA for the implementation. For each HRM assay at least three different primer sets were compared and the optimal design was chosen for the validation with genomic DNA isolated from FFPE tissues. The primers developed in the context of the present disclosure are disclosed in the following table 2:

TABLE 2

List of primer sets used for HRM and Sanger Sequencing

| Primer | Sequence (5'→3') |
|---|---|
| AKT1-2-F | CATCCCAGGCACATCTGTCC (SEQ ID NO: 1) |
| AKT1-2-R | CGCCACAGAGAAGTTGTTGAGG (SEQ ID NO: 2) |
| AKT1-HRM-ex2-FP1 | GGCGAGGGTCTGACGGGTAG (SEQ ID NO: 3) |
| AKT1-HRM-ex2-RP1 | GCCGCTCCTTGTAGCCAATGAAG (SEQ ID NO: 4) |
| BRAF-15-F | CTCTTCATAATGCTTGCTC (SEQ ID NO: 5) |
| BRAF-15-R | GTGAATACTGGGAACTATG (SEQ ID NO: 6) |
| BRAF-HRM-FP3 | ATGCTTGCTCTGATAGGAAAATGA (SEQ ID NO: 7) |
| BRAF-HRM-RP3 | ATCCAGACAACTGTTCAAACT (SEQ ID NO: 8) |
| KRAS-12,13-F | GGTGAGTTTGTATTAAAAGGTACTGG (SEQ ID NO: 9) |
| KRAS-12,13-R | GGTCCTGCACCAGTAATATGC (SEQ ID NO: 10) |
| KRAS_HRM_FP3 | CCTGCTGAAAATGACTGAATATAAACTT (SEQ ID NO: 11) |
| KRAS_HRM_RP3 | GCATATTAAAACAAGATTTACCTCTATTGT (SEQ ID NO: 12) |
| KRAS-61-F | CACTGTAATAATCCAGACTGTG (SEQ ID NO: 13) |
| KRAS-61-R | AATTACTCCTTAATGTCAGCTT (SEQ ID NO: 14) |
| KRAS-HRM61-FP10 | ACCTGTCTCTTGGATATTCTCGA (SEQ ID NO: 15) |
| KRAS-HRM61-RP10 | ATTACTCCTTAATGTCAGCTTATTATATTCA (SEQ ID NO: 16) |
| PIK3CA-7-F | AGATATTCCCATTATTATAGAGATGATTGT (SEQ ID NO: 17) |
| PIK3CA-7-R | AGCAAATCTTCTAATCCATGAGGTA (SEQ ID NO: 18) |
| PIK3CA-HRM-ex7-FP2 | GGGGAAGAAAAGTGTTTTGAAATGTG (SEQ ID NO: 19) |
| PIK3CA-HRM-ex7-RP2 | ATACTAGAGTGTCTGTGTAATCAAACAAG (SEQ ID NO: 20) |
| PIK3CA-9-F | TGAAAATGTATTTGCTTTTTCTGT (SEQ ID NO: 21) |
| PIK3CA-9-R | TGTAAATTCTGCTTTATTTATTCC (SEQ ID NO: 22) |
| PIK3CA-HRM-ex9-FP1 | TGACAAAGAACAGCTCAAAGCAA (SEQ ID NO: 23) |
| PIK3CA-HRM-ex9-RP1 | TTTTAGCACTTACCTGTGACTCCA (SEQ ID NO: 24) |
| PIK3CA-20.1-F | TTTGCTCCAAACTGACCAA (SEQ ID NO: 25) |
| PIK3CA-20.1-R | GCATGCTGTTTAATTGTGTGG (SEQ ID NO: 26) |

TABLE 2-continued

List of primer sets used for HRM and Sanger Sequencing

| Primer | Sequence (5'→3') |
|---|---|
| PIK3CA-HRM-ex20-FP2 | GCAAGAGGCTTTGGAGTATTTCA (SEQ ID NO: 27) |
| PIK3CA-HRM-ex20-RP2 | ATGCTGTTTAATTGTGTGGAAGATC (SEQ ID NO: 28) |

Primers were, in general, designed to get an amplicon with a single melting peak enhancing the sensitivity of the assay. Despite testing of 16 different primer sets the PCR products from the KRAS exon 3 HRM assay always displayed two different specific melting peaks, which both were not due to any unspecific primer dimer amplification product formation.

Since the HRM assay should be able to distinguish wildtype and mutated DNA, all samples were additionally analysed by direct Sanger Sequencing to determine the exact mutational status. Mutational status of the cell lines coincided with the literature, except KRAS exon 2 mutation analysis for LoVo (homozygous G12V) and SW 480 (heterozygous G13D), which are just inverted in our determination (Seth, R., et al., Gut 58 (2009) 1234-1241). This may be due to a mix-up of both cell lines. The difference in the melting curve behaviour of wildtype and mutated DNA was visualized by normalized, temperature-shifted curves displayed as difference plots. In each assay at least one wildtype and one mutated control DNA either isolated from cell lines, plasmids or oligonucleotides with the desired mutation were analysed.

Figure 1B:
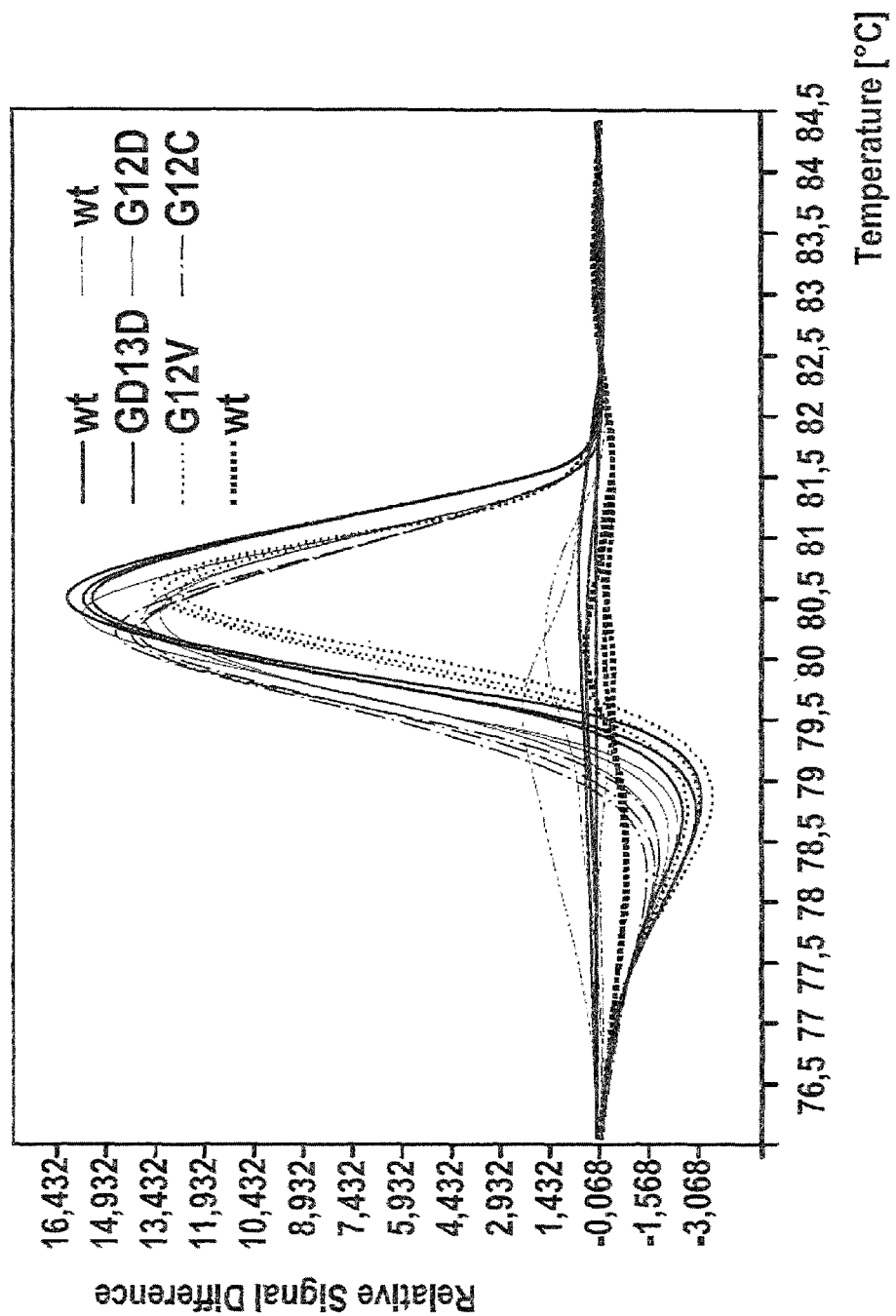
Figure 1C:
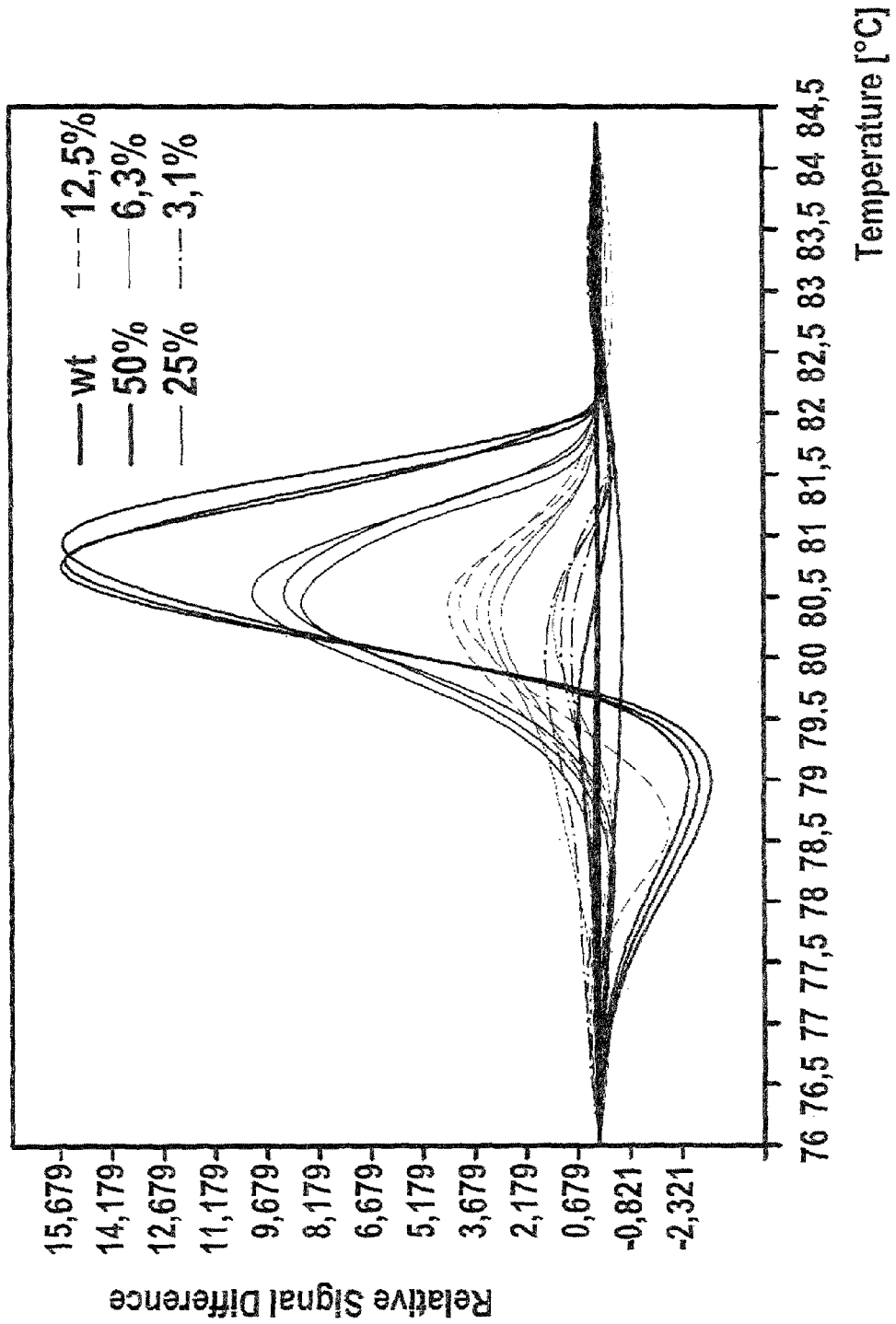
Figure 1E:
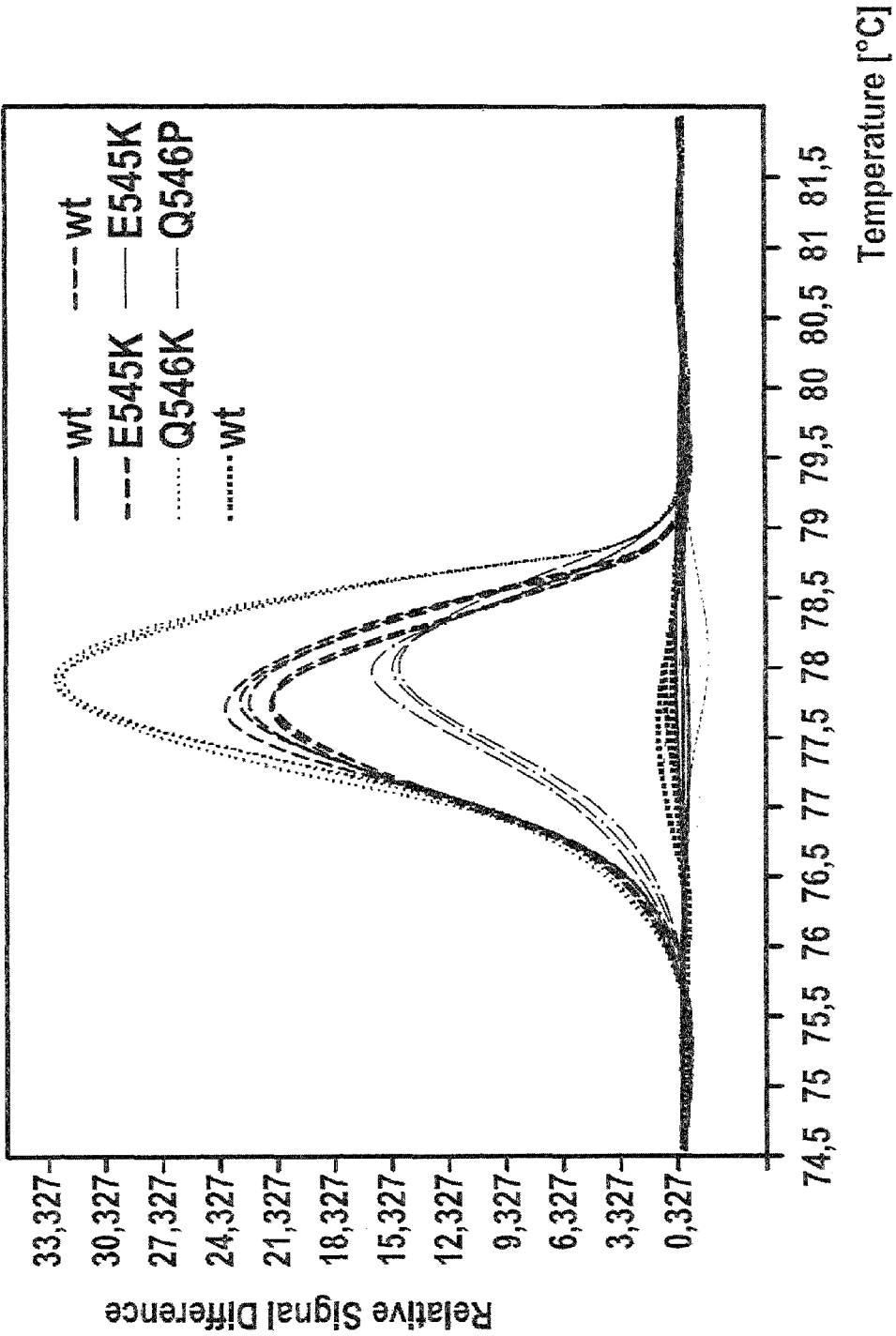
Figure 1F:
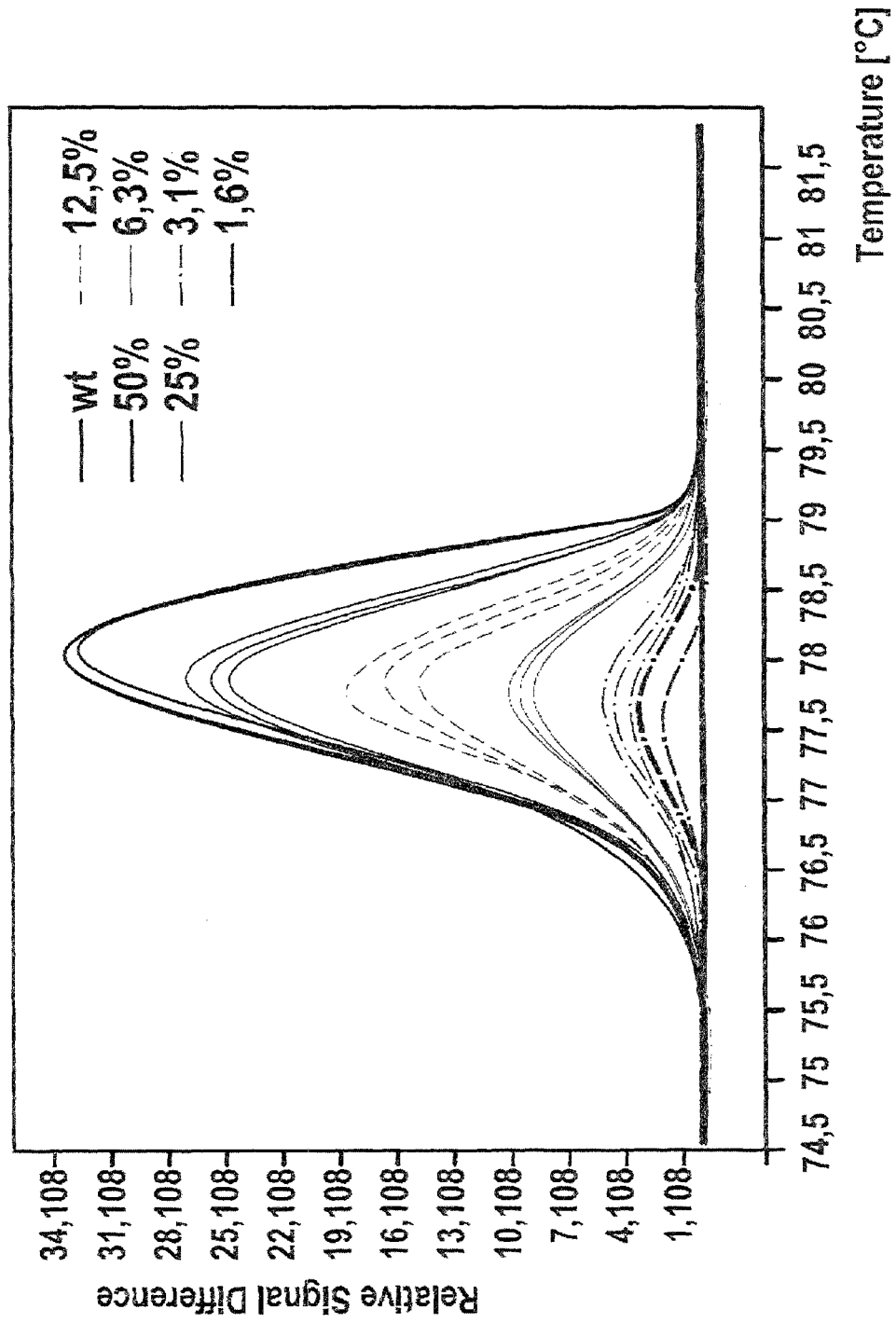

Exemplary embodiments of the present disclosure are shown in FIG. 1. It displays representative difference plots for KRAS exon 2 (FIGS. 1 A and B) and PIK3CA exon 9 (FIGS. 1 D and E) from DNA isolated from cell lines (FIGS. 1 A and D) as well as from DNA isolated from FFPE tissues (FIGS. 1 B and E). The difference in the melting behaviour of heterozygous mutations results from heteroduplex formation. Heteroduplexes melt earlier and are therefore displayed above the wildtype baseline in these illustrations (FIGS. 1 A and B). In case of homozygous mutations both DNA strands fit to each other and depending on the nucleotide difference there is either a different binding compared to wildtype sequence (FIG. 1 A) or a binding equal to wildtype.

Concerning the KRAS exon 2 assay 4/5 homozygous mutations (G12C, G12S, G12V, G13C See FIG. 1) could be differentiated from wildtype. KRAS G12R homozygous mutation was only detectable after spiking with wildtype DNA. All mutations analysed for KRAS exon 3 could only be detected in the heterozygous state. The most common V600E BRAF mutation could be differentiated from wildtype in heterozygous as well as in homozygous form. In contrast only the heterozygous E542K PIK3CA mutation could be differentiated from wildtype. Concerning the E17K AKT1 mutation there was a stronger difference between wildtype and mutation in the presence of the heterozygous state.

Regarding that some homozygous mutations were correctly reanalysed after spiking with wildtype DNA the concordance of HRM results and Sanger Sequencing for the different assays was 100%.

To determine the sensitivity of the different HRM assays dilution series of 100%, 50%, 25%, 12.5%, 6.3%, 3.1% and 1.6% of mutated template DNA in wildtype background were analysed. The sensitivities of the HRM assays were 3.1% (PIK3CA exon 9, FIG. 1 F), 6.3% (KRAS exon 2, BRAF exon 15, FIG. 1 C and data not shown) and 12.5% (KRAS exon 3, PIK3CA exon 7, PIK3CA exon 20, AKT1 exon 2) of mutated DNA which could be detected in a background of wildtype DNA.

Exclusion of BRAF, KRAS and PIK3CA Pseudogene Amplification:

Known pseudogenes are described for KRAS (McGrath, J. P., et al., Nature 304 (1983) 501-506) and BRAF (Sithanandam, G., et al, Oncogene 7 (1992) 795-799), spanning the complete exons with high homology to the gene, respectively and for PIK3CA, comprising exons 9-13 (Muller, C. I., et al., Leuk. Res. 31 (2007) 27-32). In case of BRAF, pseudogene amplification could be excluded by location of primers in the intron spanning region.

In contrast, the KRAS HRM primer set for exon 12 and 13 was partially located in the exon. Therefore potential pseudogene amplification due to the high homology between KRAS pseudogene and gene needed to become excluded. The KRAS HRM primer set flanks a region containing four nucleotides differing between the gene and pseudogene sequence. Using Sanger Sequencing there was no evidence of combined gene and pseudogene amplification. A melting curve assay using hybridization probes complementary to the KRAS gene sequence confirmed this result.

Similarly, in order to ensure a high specificity of the PIK3CA exon 9 HRM assay, primer pairs were located within a region showing sequence differences (one nucleotide exchanged and one nucleotide deleted) between gene and pseudogene. Within the chosen amplicon there was an additional single nucleotide exchange discriminating gene and pseudogene amplification. As a positive control for pseudogene amplification a second reverse primer was designed with high homology to gene and pseudogene leading to a 130 bp fragment and amplification of both. Sanger Sequencing analysis showed that PIK3CA pseudogene amplification could be excluded using the first gene specific primer pair whereas the second primer pair resulted in gene and pseudogene amplification.

Validation of the Different HRM Assays:

For the validation of the different HRM assays genomic DNA isolated from FFPE tissues from different tumor entities (colorectal cancers, endometrial cancers, melanomas, gastrointestinal stromal tumors) was used.

In case of successful amplification by the primer pairs as disclosed above, the analyses of KRAS exon 3, BRAF exon 15, PIK3CA exon 7, PIK3CA exon 9 and AKT1 exon 2 showed no differences in the results from either HRM or Sanger Sequencing. For three samples the exact mutational status of PIK3CA exon 9 could only be determined using the HRM PCR products for sequencing analyses. Using conventional methods and primer settings the sensitivity was too low to detect these mutations. The concordance from KRAS exon 2 HRM assay (205/208) and PIK3CA exon 20 HRM assay (192/193) with Sanger Sequencing was 99%, respectively. All analysed samples with discrepancy in both methods were mutated according to the HRM analyses, but wildtype using Sanger Sequencing.

HRM only allows the discrimination between wildtype and mutant samples, therefore additional Sanger Sequencing may be done when the exact mutational status is needed. KRAS exon 2 (A), 19 different KRAS mutations could be either detected in codon 12 (G12D, G12V, G12C, G12S, G12A, G12R), codon 13 (G13D, G13C, G13_V14insG), codon 14 (V14A), codon 59 (A59E), codon 60 (G60D), codon 61 (Q61H: c.183A>C, Q61H: c.183A>T, Q61K; G60G, Q61L: c.182A>T, Q61L: c.182_183AA>TG), codon 63 (E63K) or codon 66 (A66A). After validation of BRAF HRM assays four different mutations in codon 594 (D594G), codon 600 (V600E, V600K) and codon 601 (K601E) were found. The validation of the PIK3CA HRM assays showed 9 different mutations: codon 542 (E542K), codon 545 (E545K, E545G), codon 546 (Q546K, Q546R, Q546P), codon 1043 (M1043I) and codon 1047 (H1047R, H1047L). All these mutations lead to different melting behaviour compared to wildtype DNA. No mutations were found in PIK3CA exon 7 and AKT1 exon 2.

The following table summarizes the newly identified nucleic acid sequence variations with the resulting changes in the amino acid sequence of KRAS exons 2 and 3. The nucleotide that is being changed with respect to the wildtype sequence is underlined.

TABLE 3

Newly identified nucleic acid sequence variations. The underlined nucleotides represent differences from the wild type sequence.

| Amino acid level | DNA level | Seq. ID. NO: |
|---|---|---|
| exon 2, codon 13 (G13_V14insG) | c.40_41insGC GTT GGA GCT GGT GGC G<u>GC GTA</u> GGC AAG | SEQ ID NO: 31 |
| exon 2, codon 14 (V14A) | c.41T>C GTT GGA GCT GGT GGC GC<u>A</u> GGC AAG | SEQ ID NO: 32 |
| exon3, codon60 (G60D) | c.179G>A ACA GCA G<u>A</u>T CAA GAG GAG TAC AGT | SEQ ID NO: 33 |
| exon 3, codon 61 (Q61L) | c.182_183AA>TG ACA GCA GGT C<u>TG</u> GAG GAG TAC AGT | SEQ ID NO: 34 |

Accordingly, in one aspect, the present disclosure is also directed to specific hybridization probes which are capable of detecting the newly identified mutations. Such hybridization probes include oligonucleotides comprising a sequence according to SEQ. ID. NO: 31, 32, 33, 34 or their respective complements. Typically, such hybridization probes are completely identical with or complimentary to the wild type sequence of the target DNA at all position which do not correspond to the site of the mutation that shall become detected.

The length of such oligonucleotides may vary from 15 to 30 nucleotide residues, for example. These oligonucleotides are ideally completely identical or completely complementary to the corresponding gene, including its sequence variation which shall become detected. In some illustrative embodiments, such a hybridization probe may be labeled, e.g., with a fluorescent label. In some such embodiments, such a hybridization probe may be one member of a pair of FRET hybridization probes and may be used for real time PCR, as disclosed in U.S. Pat. No. 6,174,670.

As described and disclosed herein, embodiments of the instant disclosure include a new analytic method for determining the increased likelihood of a response to a targeted treatment of a cancer disease, comprising the steps of: a) isolating genomic DNA from a patient sample; b) amplifying at least one fragment of said DNA by means of PCR with a specific pair of amplification primers; c) determining, whether said amplified fragment has a wildtype sequence or comprises a mutation by means of a High Resolution Melting Analysis (HRM); and d) correlating the presence or absence of a mutation with an increased likelihood of success of said therapeutic treatment.

As disclosed herein, the term "targeted treatment" is defined as a medical treatment, characterized in that said medical treatment is selected from a number of different treatments available for the same phenotypic disease, such selection being based on the results of monitoring some previously determined biological parameter o said patient.

In some embodiments, subsequent to step c), the exact mutation is identified by means of a hybridization analysis or by means of sequencing. Hybridization analysis may be performed using the hybridization probes as disclosed above, for example. Sequencing may be done by any of the methods available in the art. In some cases, it may be useful for predicting therapeutic responses not only based on the fact that a certain region is mutated but it may also be important to know what kind of mutation occurs.

Thus, in some embodiments, the inventive method disclosed herein, under these circumstances, is a two-step process: first HRM is performed in order to identify, whether a certain gene is mutated; and second, sequencing analysis is performed but only in case HRM has revealed that the gene is mutated. Since HRM is an easy, straight forward and comparatively cheap analytical method, the number of required sequencing reactions can become reduced dramatically and the costs for drug susceptibility testing can be significantly reduced.

According to some illustrative embodiments, the patient sample is Formalin Fixed Paraffin Embedded (FFPE) tissue. If this is the case, then High Resolution Melting Analysis may be performed without any spiking of DNA. Since FFPE derived samples from cancer patients usually comprise tumor cells and non tumor cells, a hetoroduplex formation between wild type DNA originating from healthy tissue and mutated DNA from the tumor can be expected and High resolution Melting analysis can be performed.

In illustrative embodiments of the instant disclosure, the DNA fragments being analyzed may be any selected from a group comprising KRAS, exon 2, KRAS, exon 3, BRAF exon 15, PIK3CA exon 7, PIK3CA exon 9, PIK3CA exon 20, and AKT1 exon 2, for example.

For example, presence of mutations within exon 2 or exon 3 of KRAS may be indicative for a resistance against an anti-EGFR antibody based therapy, especially with respect to colorectal carcinoma. Also in particular, the presence of mutations in BRAF may be indicative of a responsiveness to RAF inhibitors such as PLX4032, especially in malignant melanoma for example. Furthermore, mutations within PIK, exon 7, 9 or 20 or AKT1 exon 2 may be helpful for the appropriate therapeutics of breast and lung carcinoma, for example.

The following examples, sequence listing, and figures are provided for the purpose of demonstrating various embodiments of the instant disclosure and aiding in an understanding of the present disclosure, the true scope of which is set forth in the appended claims. These examples are not intended to, and should not be understood as, limiting the scope or spirit of the instant disclosure in any way. It should also be understood that modifications can be made in the procedures set forth without departing from the spirit of the disclosure.

ILLUSTRATIVE EMBODIMENTS

The following comprises a list of illustrative embodiments according to the instant disclosure which represent various embodiments of the instant disclosure. These illustrative embodiments are not intended to be exhaustive or limit the disclosure to the precise forms disclosed, but rather, these illustrative embodiments are provided to aide in further describing the instant disclosure so that others skilled in the art may utilize their teachings.

1. A pair of amplification primers with oligonucleotide sequences selected from the following group of combination of sequences:

Seq. ID. No: 1 and Seq. ID. NO: 2;
   Seq. ID. No: 3 and Seq. ID. NO: 4;
   Seq. ID. No: 5 and Seq. ID. NO: 6;
   Seq. ID. No: 7 and Seq. ID. NO: 8;
   Seq. ID. No: 9 and Seq. ID. NO: 10;
   Seq. ID. No: 11 and Seq. ID. NO: 12;
   Seq. ID. No: 13 and Seq. ID. NO: 14;
   Seq. ID. No: 15 and Seq. ID. NO: 16;
   Seq. ID. No: 17 and Seq. ID. NO: 18;
   Seq. ID. No: 19 and Seq. ID. NO: 20;
   Seq. ID. No: 21 and Seq. ID. NO: 22;
   Seq. ID. No: 23 and Seq. ID. NO: 24;
   Seq. ID. No: 25 and Seq. ID. NO: 26; and
   Seq. ID. No: 27 and Seq. ID. NO: 28.

2. A composition comprising at least one pair of amplification primers according to embodiment 1.

3. A kit comprising at least one pair of amplification primers according to embodiment 1.

4. An oligonucleotide comprising a sequence selected from a group consisting of Seq. ID. NO: 31 or its complement, Seq. ID. NO: 32 or its complement, Seq. ID. NO: 33 or its complement, and Seq. ID. NO: 34 or its complement.

5. A method for determining the increased likelihood of a response to a targeted treatment of a cancer disease, comprising the steps of:

i. isolating genomic DNA from a patient sample;
   ii. amplifying at least one fragment of said DNA by means of PCR with a specific pair of amplification primers;
   iii. determining whether said amplified fragment has a wildtype sequence or comprises a mutation by means of a High Resolution Melting Analysis (HRM); and
   iv. correlating the presence or absence of a mutation with an increased likelihood of success of said targeted treatment, characterized in that said at least one fragment is selected from a group comprising of KRAS, exon 2, KRAS, Exon 3, BRAF exon 15, PIK3CA exon 7, PIK3CA exon 9, PIK3CA exon 20, and AKT1 exon 2.

6. A method according to embodiment 5, characterized in that at least one pair of amplification primers according to claim 1 is used.

7. A method according to any of embodiments 5-6, wherein prior to step d) the mutation is identified by means of a hybridization analysis or by means of sequencing.

8. A method according to any of embodiments 5-7, wherein the patient sample is Formalin Fixed Paraffin Embedded (FFPE) tissue.

9. A method according to embodiment 8, wherein High Resolution Melting Analysis is performed without any spiking of DNA.

Examples

Example 1: Design of HRM Assays

Cell Lines, Plasmids, Oligonucleotides and Patient Samples:

Seven different HRM assay were designed as can be seen from table 1 disclosed above. For the design, the cell lines as compiled in table 4 were used:

TABLE 4

Human cell lines used for the development of seven different HRM assays for KRAS exon 2; KRAS exon 3; BRAF exon 15; PIK3CA exon 7; PIK3CA exon 9; PIK3CA exon 20 and AKT1 exon 2.

| cell lines | KRAS exon 2; KRAS exon 3 | PIKCA exon 7; PIK3CA exon 9; PIK3CA exon 20 | BRAF exon 15 | AKT1 exon 2 |
|---|---|---|---|---|
| A549 | ex2: G12S (ho) | ex7: wt | | ex2: wt |
| BT-20 | | ex7: wt ex9: P539R (he) ex20: H1047R (he) | | ex2: wt |
| CaCo-2 | ex2: wt | ex7: wt | | ex2: wt |
| CaSki | | ex7: wt ex9: E545K (he) ex20: wt | | ex2: wt |
| HCT116 | ex2: G13D (he) | ex7: wt ex9: wt ex20: H1047R (he) | ex15: wt | ex2: wt |
| HT-29 | ex2: wt ex3: wt | ex7: wt | ex15: V600E (he) | ex2: wt |
| LoVo | ex2: G12V (ho) | ex7: wt | | ex2: wt |
| LS174T | ex2: G12D (he) | ex7: wt ex9: wt ex20: H1047R (he) | | ex2: wt |
| MCF-7 | | ex7: wt ex9: E545K (he) ex20: wt | | ex2: wt |
| Mel501 | | ex7: wt | ex15: V600E (he) | ex2: wt |
| Mia PaCa-2 | ex2: G12C (ho) | ex7: wt | | ex2: wt |
| NCI H460 | ex3: Q61H (ho, c.183A > T) | ex7: wt ex9: E545K (he) ex20: wt | | ex2: wt |
| NCI N417 | | ex7: wt, ex9: Q546K (he) ex20: wt | | ex2: wt |
| RPMI 8226 | ex2: G12A (he) | ex7: wt | | ex2: wt |
| OAW-42 | | ex7: wt ex9: wt ex20: H1047L (he) | | ex2: wt |
| Sk-Mel28 | | ex7: wt | ex15: V600E (ho) | ex2: wt |
| SW 480 | ex2: G13D (he) | ex7: wt | | ex2: wt |
| SW 620 | ex2: G12V (ho) | ex7: wt | | ex2: wt |
| SW 948 | | ex7: wt ex9: E542K (ho) ex20: wt | | ex2: wt |

TABLE 4-continued

Human cell lines used for the development of seven different HRM assays for KRAS exon 2; KRAS exon 3; BRAF exon 15; PIK3CA exon 7; PIK3CA exon 9; PIK3CA exon 20 and AKT1 exon 2.

| cell lines | KRAS exon 2; KRAS exon 3 | PIKCA exon 7; PIK3CA exon 9; PIK3CA exon 20; | BRAF exon 15 | AKT1 exon 2 |
|---|---|---|---|---|
| T47D | | ex7: wt<br>ex9: wt<br>ex20: H1047R (he) | | ex2: wt |

Used abbreviations: ex = exon, he = heterozygous, ho = homozygous, wt = wildtype All cell lines were grown under standard conditions. Determination of mutation status was done by Sanger Sequencing. Cell lines without description of mutation status were not determined.

Plasmids with human genomic DNA fragments containing KRAS mutations were either obtained from Roche (Pleasanten, Calif., USA) or generated by cloning the relevant fragments into the pCR-4 vector by using the TOPO TA Cloning Kit for Sequencing (Invitrogen, Karisruhe, Germany) according to manufacturer's instructions. For rare mutations (AKT1: E17K, PIK3CA: C420R), whole PCR products were ordered (Metabion, Martinsried, Germany).

The HRM mutation assays were validated on routinely used FFPE tissues (colorectal cancers, endometrial cancers, melanomas, gastrointestinal stromal tumors). Analysed sample numbers ranged from 131 to 205 depending on the assay. Ethical approval for this research was obtained from the local ethical committee.

Genomic DNA from cell lines was isolated using the QIAamp DNA Mini Kit (Qiagen, Hilden, Germany) according to manufacturer's protocols. For DNA isolation from FFPE tissue, a tumor area was marked on the hematoxylin and eosin (H&E) stained sections and macrodissected on corresponding unstained 10 µm thick slides for subsequent DNA isolation. DNA purification was performed using the BioRobot M48 Robotic Workstation and the corresponding MagAttract DNA Mini M48 Kit (Qiagen) following the manufacturer's instructions. DNA quantity was assessed spectrophotometrically using the NanoDrop ND 1000 (Peqlab, Erlangen, Germany) and quality of genomic DNA was confirmed by agarose gel electrophoresis. Extracted DNA was temporary stored at 4° C. and long-term stored at −20° C. or −80° C. High Resolution Melting Analyses (HRM). HRM analyses were performed on a LightCycler™ 480 (Roche Diagnostics, Mannheim, Germany). Each run included mutated and wildtype DNA as controls as shown in tables 4 and 5.

TABLE 5

Plasmids used for the development of KRAS HRM assays and melting curve analysis by using hybridization probes to exclude any KRAS pseudogene amplification.

| Plasmids | KRAS mutation status | Reference |
|---|---|---|
| pCR-4 E63K 27 | E63K (c.187G > A) | this work |
| pCR-4 A59E 35 | A59E (c.176C > A) | this work |
| pCR-4 Q61H (CAC) A27 | Q61H (c.183A > C) | this work |
| pCR-4 Q61L (CTA) B6 | Q61L (c.182A > T) | this work |
| pCR-4 Q61L (CTG) C3 | Q61L (c.182_183AA > TG) | this work |

TABLE 5-continued

Plasmids used for the development of KRAS HRM assays and melting curve analysis by using hybridization probes to exclude any KRAS pseudogene amplification.

| Plasmids | KRAS mutation status | Reference |
|---|---|---|
| pK12C1 | G12R (c.34G > C) | Roche (Pleasanton, CA, USA) |
| pK13T1 | G13C (c.37G > T) | Roche (Pleasanton, CA, USA) |

For each assay at least three different primer sets (HPLC purified, Sigma Aldrich, Munich, Germany) were selected to flank the hot spot mutation regions of the gene. Amplicon lengths ranged from 100 bp to 186 bp depending on the HRM assay. All designed primers are compiled in table 2 as disclosed in the specification above.

Each reaction mixture contained 10 ng of genomic DNA or 10 fg of plasmid DNA or 0.2-2 fM oligonucleotides, 200 nmol/L of each primer, 10 pt of LightCycler LC480 High Resolution Melting Master (Roche Diagnostics), 3.5 mmol/L $MgCl_2$ or 3.0 mmol/L $MgCl_2$ in the case of PIK3CA exon 20 and AKT1 exon 2 assay and A. dest. to a final volume of 20 µl. All reactions were routinely performed in triplicates. PCR and melting curve conditions were used according to manufacturer's instructions. Annealing temperatures were 60° C. for all HRM assays except the following: BRAF exon 15 (59° C.), KRAS exon 3 (58° C.) and AKT1 exon 2 (63° C.). The melting curves were analysed by Gene Scanning software (Roche Diagnostics) with normalized, temperature-shifted curves displayed finally as a difference plot. Either genomic wildtype DNA isolated from cell lines or plasmid DNA was used for normalization.

In case of significant differences of the fluorescence level for all triplicates, which were not in the range of variation detected for wildtype control, samples were considered as mutated. The HRM method depends on heteroduplex formation, so statistically rare homozygous mutations might not be detected. For this purpose, all control DNA samples negative on initial screening were spiked with wildtype DNA and reanalysed. FFPE tissues were not spiked with wildtype DNA as after macrodissection usually few normal tissue and/or stromal cells are included and allow heteroduplex formation. To determine the sensitivity of HRM assays mutated DNA or oligonucleotides containing the mutation of interest were serially diluted with wildtype DNA.

Sanger Sequencing.

Sanger Sequencing analyses were performed from all samples to determine the mutation status and to verify the HRM results. Depending on the HRM assay design, verification of results were either done from conventionally amplified DNA fragments using Platinum Taq DNA polymerase (Invitrogen) or from fragments amplified by real-time PCR for HRM analysis. The latter PCR products could be directly used for sequencing analyses, whereas conventionally amplified PCR products were checked for the right fragment length by agarose gel electrophoresis and purified using S-300 HR MicroSpin Columns (Amersham Pharmacia Biotech, Freiburg, Germany) or polyethylene glycol precipitation. Purified PCR products were sequenced using BigDye Terminator v1.1 Cycle Sequencing kit. Sequences were run on an ABI Prism 3130 automated sequencer and data were manually edited using Sequencer analysis software (all Applied Biosystems, Darmstadt, Germany).

Melting Curve Analysis by Using Hybridization Probes.

A melting curve assay using hybridization probes was designed to exclude KRAS pseudogene amplification. The Hybridization probes used were:

KRAS1, which was a 3' Fluorescein probe, comprising the nucleotide sequence:

TAGGCAAGAGTGCCTTGACGA,          (SEQ ID NO: 29)

and

KRAS2 which was 5' Red640 labeled probe and a 3' terminal phosphate block, comprising the nucleotide sequence:

(SEQ ID NO: 30)
ACAGCTAATTCAGAATCATTTTGTGGACGAATATGATCCA.

The probes were designed with the LightCycler Probe Design 2.0 software (Roche Diagnostics) and tested for their specificity as described above. An asymmetric PCR was performed by using LightCycler Probes Master (Roche Diagnostics) according to manufacturer's instructions. Briefly, 10 ng genomic template DNA, 10 fg plasmid DNA or 0.2 μM KRAS pseudogene control were mixed with 0.2 μM hybridization probes, 0.075 μM KRAS_HRM_FP3, 0.5 μM KRAS_HRM_RP3 and A. dest. to a final volume of 20 μl. The whole PCR products for the KRAS pseudogene control were acquired by purchase (Metabion). PCR and melting curve conditions were used according to manufacturer's instructions.

All references cited in this specification are herewith incorporated by reference with respect to their entire disclosure content and the disclosure content specifically mentioned in this specification.

While this disclosure has been described as having an exemplary design, the present disclosure may be further modified within the spirit and scope of this disclosure. This application is therefore intended to cover any variations, uses, or adaptations of the disclosure using its general principles. Further, this application is intended to cover such departures from the present disclosure as come within the known or customary practice in the art to which this disclosure pertains.

What is claimed is:

1. A method of treating a cancer patient comprising:
   i) isolating genomic DNA from a sample from the cancer patient;
   ii) amplifying a fragment of said DNA by means of PCR with a specific pair of amplification primers, thereby forming an amplified fragment;
   iii) determining that said amplified fragment does not comprise a G13_V14A or G60D mutation in the KRAS gene by means of a High Resolution Melting Analysis (HRM) and DNA sequencing; and
   iv) treating the cancer patient with an anti-EGFR targeted treatment.

2. The method of claim 1, wherein in step ii, the amplification primers comprise one or more sequences selected from the group consisting of SEQ ID NOs: 9-16.

3. The method of claim 1, wherein the sample is Formalin Fixed Paraffin Embedded (FFPE) tissue.

4. The method of claim 1, wherein said step of determining comprises performing High Resolution Melting Analysis without any spiking of DNA.

5. The method of claim 1, wherein said step of determining comprises comparing HRM analysis results of the amplified fragment to a control.

6. The method of claim 5, wherein the control comprises HRM analysis results of a wildtype sample.

7. The method of claim 1, wherein HRM is performed using a probe selected from a group consisting of SEQ ID NO: 31 or its complement, SEQ ID NO: 32 or its complement, and SEQ ID NO: 33 or its complement.

8. The method of claim 1, wherein the cancer patient has colorectal cancer.

9. The method of claim 1, wherein the anti-EGFR targeted treatment is an anti-EGFR antibody therapy.

10. The method of claim 1, wherein the anti-EGFR targeted treatment is panitumumab or cetuximab.

* * * * *

SEQUENCE LISTING

```
<160> NUMBER OF SEQ ID NOS: 34

<210> SEQ ID NO 1
<211> LENGTH: 20
<212> TYPE: DNA
<213> ORGANISM: Artificial Sequence
<220> FEATURE:
<223> OTHER INFORMATION: single stranded

<400> SEQUENCE: 1
catcccaggc acatctgtcc                                               20

<210> SEQ ID NO 2
<211> LENGTH: 22
<212> TYPE: DNA
<213> ORGANISM: Artificial Sequence
<220> FEATURE:
<223> OTHER INFORMATION: single stranded

<400> SEQUENCE: 2
cgccacagag aagttgttga gg                                            22

<210> SEQ ID NO 3
<211> LENGTH: 20
<212> TYPE: DNA
<213> ORGANISM: Artificial Sequence
<220> FEATURE:
<223> OTHER INFORMATION: single stranded

<400> SEQUENCE: 3
ggcgagggtc tgacgggtag                                               20

<210> SEQ ID NO 4
<211> LENGTH: 23
<212> TYPE: DNA
<213> ORGANISM: Artificial Sequence
<220> FEATURE:
<223> OTHER INFORMATION: single stranded

<400> SEQUENCE: 4
gccgctcctt gtagccaatg aag                                           23
```

```
<210> SEQ ID NO 5
<211> LENGTH: 19
<212> TYPE: DNA
<213> ORGANISM: Artificial Sequence
<220> FEATURE:
<223> OTHER INFORMATION: single stranded

<400> SEQUENCE: 5
ctcttcataa tgcttgctc                                                19

<210> SEQ ID NO 6
<211> LENGTH: 19
<212> TYPE: DNA
<213> ORGANISM: Artificial Sequence
<220> FEATURE:
<223> OTHER INFORMATION: single stranded

<400> SEQUENCE: 6
gtgaatactg ggaactatg                                                19

<210> SEQ ID NO 7
<211> LENGTH: 24
<212> TYPE: DNA
<213> ORGANISM: Artificial Sequence
<220> FEATURE:
<223> OTHER INFORMATION: single stranded

<400> SEQUENCE: 7
atgcttgctc tgataggaaa atga                                          24

<210> SEQ ID NO 8
<211> LENGTH: 21
<212> TYPE: DNA
<213> ORGANISM: Artificial Sequence
<220> FEATURE:
<223> OTHER INFORMATION: single stranded

<400> SEQUENCE: 8
atccagacaa ctgttcaaac t                                             21

<210> SEQ ID NO 9
<211> LENGTH: 26
<212> TYPE: DNA
<213> ORGANISM: Artificial Sequence
<220> FEATURE:
<223> OTHER INFORMATION: single stranded

<400> SEQUENCE: 9
ggtgagtttg tattaaaagg tactgg                                        26

<210> SEQ ID NO 10
<211> LENGTH: 21
<212> TYPE: DNA
<213> ORGANISM: Artificial Sequence
<220> FEATURE:
<223> OTHER INFORMATION: single stranded

<400> SEQUENCE: 10
ggtcctgcac cagtaatatg c                                             21

<210> SEQ ID NO 11
<211> LENGTH: 28
<212> TYPE: DNA
<213> ORGANISM: Artificial Sequence
<220> FEATURE:
<223> OTHER INFORMATION: single stranded
```

<400> SEQUENCE: 11
cctgctgaaa atgactgaat ataaactt                                     28

<210> SEQ ID NO 12
<211> LENGTH: 30
<212> TYPE: DNA
<213> ORGANISM: Artificial Sequence
<220> FEATURE:
<223> OTHER INFORMATION: single stranded

<400> SEQUENCE: 12
gcatattaaa acaagattta cctctattgt                                   30

<210> SEQ ID NO 13
<211> LENGTH: 22
<212> TYPE: DNA
<213> ORGANISM: Artificial Sequence
<220> FEATURE:
<223> OTHER INFORMATION: single stranded

<400> SEQUENCE: 13
cactgtaata atccagactg tg                                           22

<210> SEQ ID NO 14
<211> LENGTH: 22
<212> TYPE: DNA
<213> ORGANISM: Artificial Sequence
<220> FEATURE:
<223> OTHER INFORMATION: single stranded

<400> SEQUENCE: 14
aattactcct taatgtcagc tt                                           22

<210> SEQ ID NO 15
<211> LENGTH: 23
<212> TYPE: DNA
<213> ORGANISM: Artificial Sequence
<220> FEATURE:
<223> OTHER INFORMATION: single stranded

<400> SEQUENCE: 15
acctgtctct tggatattct cga                                          23

<210> SEQ ID NO 16
<211> LENGTH: 31
<212> TYPE: DNA
<213> ORGANISM: Artificial Sequence
<220> FEATURE:
<223> OTHER INFORMATION: single stranded

<400> SEQUENCE: 16
attactcctt aatgtcagct tattatattc a                                 31

<210> SEQ ID NO 17
<211> LENGTH: 30
<212> TYPE: DNA
<213> ORGANISM: Artificial Sequence
<220> FEATURE:
<223> OTHER INFORMATION: single stranded

<400> SEQUENCE: 17
agatattccc attattatag agatgattgt                                   30

<210> SEQ ID NO 18
<211> LENGTH: 25

<212> TYPE: DNA
<213> ORGANISM: Artificial Sequence
<220> FEATURE:
<223> OTHER INFORMATION: single stranded

<400> SEQUENCE: 18
agcaaatctt ctaatccatg aggta                                      25

<210> SEQ ID NO 19
<211> LENGTH: 26
<212> TYPE: DNA
<213> ORGANISM: Artificial Sequence
<220> FEATURE:
<223> OTHER INFORMATION: single stranded

<400> SEQUENCE: 19
ggggaagaaa agtgttttga aatgtg                                     26

<210> SEQ ID NO 20
<211> LENGTH: 29
<212> TYPE: DNA
<213> ORGANISM: Artificial Sequence
<220> FEATURE:
<223> OTHER INFORMATION: single stranded

<400> SEQUENCE: 20
atactagagt gtctgtgtaa tcaaacaag                                  29

<210> SEQ ID NO 21
<211> LENGTH: 24
<212> TYPE: DNA
<213> ORGANISM: Artificial Sequence
<220> FEATURE:
<223> OTHER INFORMATION: single stranded

<400> SEQUENCE: 21
tgaaaatgta tttgcttttt ctgt                                       24

<210> SEQ ID NO 22
<211> LENGTH: 24
<212> TYPE: DNA
<213> ORGANISM: Artificial Sequence
<220> FEATURE:
<223> OTHER INFORMATION: single stranded

<400> SEQUENCE: 22
tgtaaattct gctttattta ttcc                                       24

<210> SEQ ID NO 23
<211> LENGTH: 23
<212> TYPE: DNA
<213> ORGANISM: Artificial Sequence
<220> FEATURE:
<223> OTHER INFORMATION: single stranded

<400> SEQUENCE: 23
tgacaaagaa cagctcaaag caa                                        23

<210> SEQ ID NO 24
<211> LENGTH: 24
<212> TYPE: DNA
<213> ORGANISM: Artificial Sequence
<220> FEATURE:
<223> OTHER INFORMATION: single stranded

<400> SEQUENCE: 24
ttttagcact tacctgtgac tcca                               24

<210> SEQ ID NO 25
<211> LENGTH: 19
<212> TYPE: DNA
<213> ORGANISM: Artificial Sequence
<220> FEATURE:
<223> OTHER INFORMATION: single stranded

<400> SEQUENCE: 25
tttgctccaa actgaccaa                                     19

<210> SEQ ID NO 26
<211> LENGTH: 21
<212> TYPE: DNA
<213> ORGANISM: Artificial Sequence
<220> FEATURE:
<223> OTHER INFORMATION: single stranded

<400> SEQUENCE: 26
gcatgctgtt taattgtgtg g                                  21

<210> SEQ ID NO 27
<211> LENGTH: 23
<212> TYPE: DNA
<213> ORGANISM: Artificial Sequence
<220> FEATURE:
<223> OTHER INFORMATION: single stranded

<400> SEQUENCE: 27
gcaagaggct ttggagtatt tca                                23

<210> SEQ ID NO 28
<211> LENGTH: 25
<212> TYPE: DNA
<213> ORGANISM: Artificial Sequence
<220> FEATURE:
<223> OTHER INFORMATION: single stranded

<400> SEQUENCE: 28
atgctgttta attgtgtgga agatc                              25

<210> SEQ ID NO 29
<211> LENGTH: 21
<212> TYPE: DNA
<213> ORGANISM: Artificial Sequence
<220> FEATURE:
<223> OTHER INFORMATION: single stranded

<400> SEQUENCE: 29
taggcaagag tgccttgacg a                                  21

<210> SEQ ID NO 30
<211> LENGTH: 40
<212> TYPE: DNA
<213> ORGANISM: Artificial Sequence
<220> FEATURE:
<223> OTHER INFORMATION: single stranded

<400> SEQUENCE: 30
acagctaatt cagaatcatt ttgtggacga atatgatcca              40

<210> SEQ ID NO 31
<211> LENGTH: 27
<212> TYPE: DNA
<213> ORGANISM: Artificial Sequence -continued

```
<220> FEATURE:
<223> OTHER INFORMATION: single stranded
<220> FEATURE:
<221> NAME/KEY: misc_feature
<223> OTHER INFORMATION: exon 2, codon 13; G13_V14insG; c.40_41insGCG

<400> SEQUENCE: 31
gttggagctg gtggcggcgt aggcaag                                              27

<210> SEQ ID NO 32
<211> LENGTH: 24
<212> TYPE: DNA
<213> ORGANISM: Artificial Sequence
<220> FEATURE:
<223> OTHER INFORMATION: single stranded
<220> FEATURE:
<221> NAME/KEY: misc_feature
<223> OTHER INFORMATION: exon 2, codon 14; V14A; c.41T>C

<400> SEQUENCE: 32
gttggagctg gtggcgcagg caag                                                 24

<210> SEQ ID NO 33
<211> LENGTH: 24
<212> TYPE: DNA
<213> ORGANISM: Artificial Sequence
<220> FEATURE:
<223> OTHER INFORMATION: single stranded
<220> FEATURE:
<221> NAME/KEY: misc_feature
<223> OTHER INFORMATION: exon3, codon60; G60D;  c.179G>A

<400> SEQUENCE: 33
acagcagatc aagaggagta cagt                                                 24

<210> SEQ ID NO 34
<211> LENGTH: 24
<212> TYPE: DNA
<213> ORGANISM: Artificial Sequence
<220> FEATURE:
<223> OTHER INFORMATION: single stranded
<220> FEATURE:
<221> NAME/KEY: misc_feature
<223> OTHER INFORMATION: exon 3, codon 61; Q61L; c.182_183AA>TG

<400> SEQUENCE: 34
acagcaggtc tggaggagta cagt                                                 24
```